(12) United States Patent
Eizirik et al.

(10) Patent No.: US 8,425,878 B2
(45) Date of Patent: Apr. 23, 2013

(54) PLASMA MEMBRANE BIOMARKERS PREFERENTIALLY EXPRESSED IN PANCREATIC BETA CELLS USEFUL IN IMAGING OR TARGETING BETA CELLS

(75) Inventors: Decio L. Eizirik, Dilbeek (BE); Daisy Flamez, Lennik (BE); Isabelle Salmon, Bruxelles (BE); Alix Berton, Yens (CH); Isabelle Roland, Namur (BE); Daniel Marechal, Louveigne (BE); Marie-Claire Beckers, Beyne-Heusay (BE); Leroy Hood, Seattle, WA (US); Nathan Goodman, Lake Forest Park, WA (US); Burak Kutlu, Seattle, WA (US)

(73) Assignee: Universite Libre de Bruxelles, Brussels (BE)

( * ) Notice: Subject to any disclaimer, the term of this patent is extended or adjusted under 35 U.S.C. 154(b) by 181 days.

(21) Appl. No.: 12/735,731

(22) PCT Filed: Feb. 13, 2009

(86) PCT No.: PCT/EP2009/051721
§ 371 (c)(1),
(2), (4) Date: Aug. 11, 2010

(87) PCT Pub. No.: WO2009/101181
PCT Pub. Date: Aug. 20, 2009

(65) Prior Publication Data
US 2010/0322850 A1 Dec. 23, 2010

Related U.S. Application Data

(60) Provisional application No. 61/066,068, filed on Feb. 14, 2008.

(51) Int. Cl.
*A61K 49/00* (2006.01)
(52) U.S. Cl.
USPC .................................. 424/9.1; 424/9.34
(58) Field of Classification Search ................ None
See application file for complete search history.

(56) References Cited

FOREIGN PATENT DOCUMENTS

| WO | WO 2004/046355 | 6/2004 |
|---|---|---|
| WO | WO 2009/101181 A2 | 8/2009 |

OTHER PUBLICATIONS

Kim J.W. et al., Short sequence-paper: Cloning and expression of human cDNA encoding Naq,Kq-ATPase g-subunit, Biochimica et Biophysica Acta, 1997, vol. 1350, pp. 133-135.*
Floyd R.V. et al., Differential cellular expression of FXYD1 (phospholemman) and FXYD2 (gamma subunit of Na, K-ATPase) in normal human tissues: A study using high density human tissue microarrays, Annals of Anatomy, 2010, vol. 192, pp. 7-16.*
Flamez D. et al., A genomic-based approach identifies FXYD domain containing ion transport regulator 2 (FXYD2)ya as a pancreatic beta cell-specific biomarker, Diabetologia, 2010, vol. 53, pp. 1372-1383.*
PCT International Search Report for International Application No. PCT/EP2009/051721, dated Nov. 3, 2009.
Flamez et al., "A platform for the identification and validation of beta cell specific membrane biomarkers," Diabetologia, Sep. 2008, p. S141, vol. 51, No. Suppl. 1, and 44th Annual Meeting of the European Association for the Study of Diabetes; Rome, Italy, Sep. 8-11, 2008 abstract.
Elena Arystarkhova et al,. "Splice Variants of the Gamma Subunit (FXYD2) and Their Significance in Regulation fo the Na, K-ATPase in Kidney," Journal of Bioenergetics and Biomembranes, Kluwer, Dec. 1, 2005, pp. 381-386, vol. 37, No. 6.
PCT International Preliminary Report on Patentability for International Application No. PCT/EP2009/051721, mailed Aug. 17, 2010.

* cited by examiner

*Primary Examiner* — Jon P Weber
*Assistant Examiner* — Satyendra Singh
(74) *Attorney, Agent, or Firm* — TraskBritt

(57) ABSTRACT

The present invention is directed to the identification of a biomarker specifically located in the plasma membrane of pancreatic beta cells. It was selected by a Systems Biology approach on Massively Parallel Signal Sequencing datasets obtained in human islets and Affymetrix microarray datasets on human islets, purified rat primary beta and non beta cells and insulinoma cells. Based on a set of specific features the biomarker is a unique candidate for imaging and targeting strategies to study the pancreatic beta cell mass in health and disease (T1 D, T2D, pancreatic cancers, obesity, islet transplantation, beta cell regeneration). The five specific features of the selected biomarkers are: 1) Preferentially expressed in pancreatic islets as compared to surrounding tissues; 2) Higher expression in pancreatic beta cells than in pancreatic alpha cells or than in other islet non-beta cells; 3) Expression levels in pancreatic beta cells are higher or comparable to glucokinase which is an enzyme specifically expressed in the pancreatic beta cell; 4) Located in the membrane and as such targetable with antibodies, peptides or small molecules which allows imaging, targeting and immunohistochemistry; and 5) Expression is not induced during the process of inflammation of the beta cell mass and the protein is not enriched in T-cells and dendritic cells or in other cells participating in the inflammation process.

4 Claims, 19 Drawing Sheets

Figure 1

```
         SIGNAL   |    EXTRACELLULAR    |   TM   |   CYTOPLASMIC
                           FXYD

FXYD1 MASLGHILVFCVGLLITMAKAESPK-EHDPFTYDYQSLQIGGLVIAGILFILGILIVLSRRCRCKFNQQQRTGEPDEEGTFRSSIRRLSTRRR--
FXYD2 -------------MTGLSMDGGGSPKGDVDPFYYDYETVRNGGLIFAGLAFIVGLLLLLSRRFRCGGNKKRRQINEDEP----------------
FXYD3 MQKVTLGLLVFLAGFPVLDANDLEDKNSPFYYDWHSLQVGGLICAMGIIIVMSAKCKCKFGQKSGHHPGETPPLITPGSAQS--------------
FXYD4 MERVTLALLLLAGLTALEANDPFFYYDKNLQLSGLICGLLAIAGIAAVLFITGIIILTSGK--CR-QLSRLCRNHCR------------------
FXYD5 *LSERPSPSTDVQTDPQTLKPSGFHEDDPFFFYDEHTLRKRGLLVAAVLFITGIIILTSGK--CR-QLSRLCRNHCR------------------
FXYD6 MELVLVFLCSLLAPMVLASAAEKEKEMDPFHYDYQTLRIGGLVFAVVLFSVGILLLILSRRCKCSFNQKPRAPGDEEAQVENLITANATEPQKAEN
FXYD7 -----------MATPTQTPTKAPEEPDPFFYYDYNTVQTVGMTLATILFLLGILIVISKKVKCRKADSRSESPTCKSCKSELPSSAPGGGGV---

*N-terminal extension of FXYD5:

MSPSGRLCLLITVGLILPTRGQTLKDTTSSSSADSTIMDIQVPTRAPDAVYTELQPTSPTPTWPADETPQPQTQTQQLEGTDGPLVTDPETHKSTKAAHPTD
DTTT
```

Figure 2A

γa peptide:
Human   MTGLSMDGGGS
Rat     MTELSANHGGS
Mouse   MAGEISDLSANSGGS

γb peptide: Human=Rat=Mouse
MDRWYLGGS

Figure 2B

```
HUMAN FXYD2-GAMMA-A   MTGLSMDGGGSPKGDVDPFYDYETVRNGGLIFAGLAFIVGLLILLSRRF
HUMAN FXYD2-GAMMA-B   ---MDRWYLGGSPKGDVDPFYDYETVRNGGLIFAGLAFIVGLLILLSRRF
HUMAN FXYD2-GAMMA-C   MTGLSMDGGGSPKGDVDPFYYGKPGPLRTLPEPSGPLPPSSGLSQPQVHA

HUMAN FXYD2-GAMMA-A   RCGGNKKRRQINEDEP---------------------------------
HUMAN FXYD2-GAMMA-B   RCGGNKKRRQINEDEP---------------------------------
HUMAN FXYD2-GAMMA-C   LCPLSPLVTTGCCGQAAERDSCWERPPIPLLLPSLSGDYETVRNGGLIFA

HUMAN FXYD2-GAMMA-A   -------------------------------------------------
HUMAN FXYD2-GAMMA-B   -------------------------------------------------
HUMAN FXYD2-GAMMA-C   GLAFIVGLLILLSKWGGLQGRGADQGTSLLKAAEQAGFRELPREG
```

A                           B

← 19 kDa

← 6,4 kDa

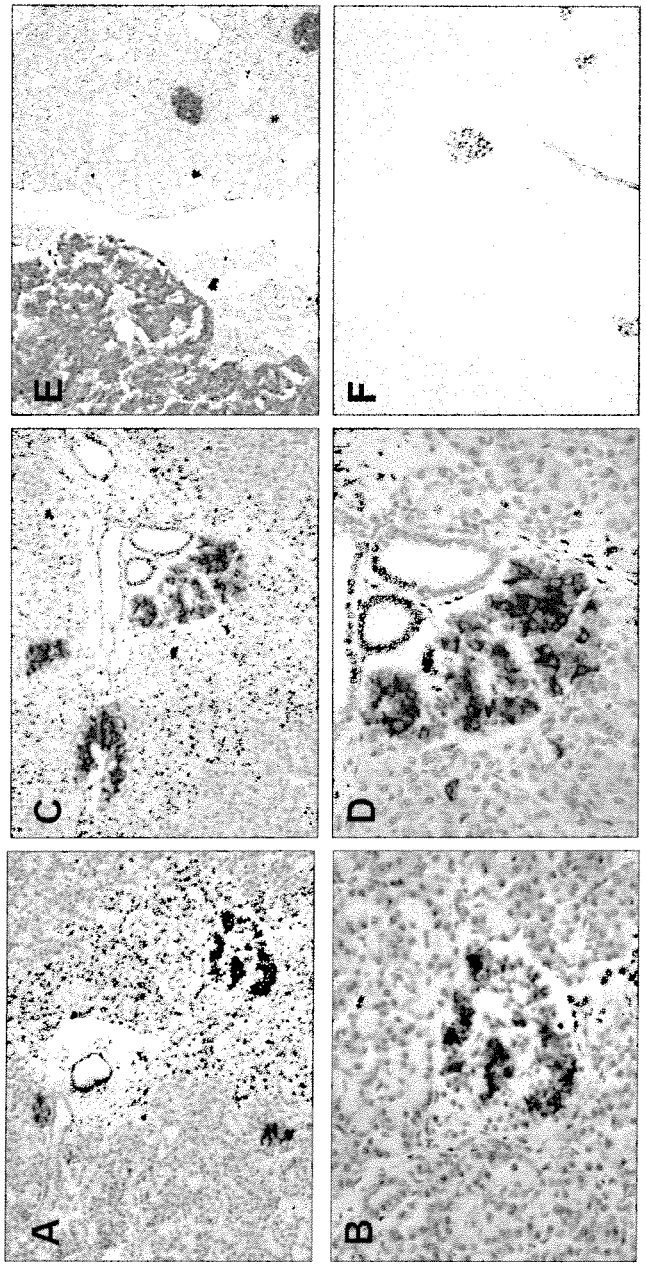

SEQUENCE LISTING

```
<160> NUMBER OF SEQ ID NOS: 10

<210> SEQ ID NO 1
<211> LENGTH: 11
<212> TYPE: PRT
<213> ORGANISM: Artificial
<220> FEATURE:
<223> OTHER INFORMATION: To raise antibodies against FXYD2-GAMMA-A

<400> SEQUENCE: 1

Met Thr Gly Leu Ser Met Asp Gly Gly Gly Ser
1               5                   10

<210> SEQ ID NO 2
<211> LENGTH: 15
<212> TYPE: PRT
<213> ORGANISM: Artificial
<220> FEATURE:
<223> OTHER INFORMATION: To raise antibodies against FXYD2-GAMMA-A

<400> SEQUENCE: 2

Met Thr Gly Leu Ser Met Asp Gly Gly Gly Ser Pro Lys Gly Asp
1               5                   10                  15

<210> SEQ ID NO 3
<211> LENGTH: 28
<212> TYPE: PRT
<213> ORGANISM: Artificial
<220> FEATURE:
<223> OTHER INFORMATION: To raise antibodies against FXYD2-GAMMA-A

<400> SEQUENCE: 3

Met Thr Gly Leu Ser Met Asp Gly Gly Gly Ser Pro Lys Gly Asp Val
1               5                   10                  15

Asp Pro Phe Tyr Tyr Asp Tyr Glu Thr Val Arg Asn
            20                  25

<210> SEQ ID NO 4
```

```
<211> LENGTH: 9
<212> TYPE: PRT
<213> ORGANISM: Artificial
<220> FEATURE:
<223> OTHER INFORMATION: To raise antibodies against FXYD2-GAMMA-B

<400> SEQUENCE: 4

Met Asp Arg Trp Tyr Leu Gly Gly Ser
1               5

<210> SEQ ID NO 5
<211> LENGTH: 66
<212> TYPE: PRT
<213> ORGANISM: Artificial
<220> FEATURE:
<223> OTHER INFORMATION: To raise Antibodies against FXYD2-GAMMA-C

<400> SEQUENCE: 5

Gly Lys Pro Gly Pro Leu Arg Thr Leu Pro Glu Pro Ser Gly Pro Leu
1               5                   10                  15

Pro Pro Ser Ser Gly Leu Ser Gln Pro Gln Val His Ala Leu Cys Pro
            20                  25                  30

Leu Ser Pro Leu Val Thr Thr Gly Cys Cys Gly Gln Ala Ala Glu Arg
        35                  40                  45

Asp Ser Cys Trp Glu Arg Pro Pro Ile Pro Leu Leu Leu Pro Ser Leu
    50                  55                  60

Ser Gly
65

<210> SEQ ID NO 6
<211> LENGTH: 66
<212> TYPE: PRT
<213> ORGANISM: Homo sapiens

<400> SEQUENCE: 6

Met Thr Gly Leu Ser Met Asp Gly Gly Gly Ser Pro Lys Gly Asp Val
1               5                   10                  15

Asp Pro Phe Tyr Tyr Asp Tyr Glu Thr Val Arg Asn Gly Gly Leu Ile
            20                  25                  30

Phe Ala Gly Leu Ala Phe Ile Val Gly Leu Leu Ile Leu Leu Ser Arg
        35                  40                  45

Arg Phe Arg Cys Gly Gly Asn Lys Lys Arg Arg Gln Ile Asn Glu Asp
    50                  55                  60

Glu Pro
65

<210> SEQ ID NO 7
<211> LENGTH: 64
<212> TYPE: PRT
<213> ORGANISM: Homo sapiens

<400> SEQUENCE: 7

Met Asp Arg Trp Tyr Leu Gly Gly Ser Pro Lys Gly Asp Val Asp Pro
1               5                   10                  15

Phe Tyr Tyr Asp Tyr Glu Thr Val Arg Asn Gly Gly Leu Ile Phe Ala
            20                  25                  30

Gly Leu Ala Phe Ile Val Gly Leu Leu Ile Leu Leu Ser Arg Arg Phe
        35                  40                  45

Arg Cys Gly Gly Asn Lys Lys Arg Arg Gln Ile Asn Glu Asp Glu Pro
    50                  55                  60
```

```
<210> SEQ ID NO 8
<211> LENGTH: 145
<212> TYPE: PRT
<213> ORGANISM: Homo sapiens

<400> SEQUENCE: 8

Met Thr Gly Leu Ser Met Asp Gly Gly Ser Pro Lys Gly Asp Val
1               5                   10                  15

Asp Pro Phe Tyr Tyr Gly Lys Pro Gly Pro Leu Arg Thr Leu Pro Glu
            20                  25                  30

Pro Ser Gly Pro Leu Pro Pro Ser Ser Gly Leu Ser Gln Pro Gln Val
        35                  40                  45

His Ala Leu Cys Pro Leu Ser Pro Leu Val Thr Thr Gly Cys Cys Gly
    50                  55                  60

Gln Ala Ala Glu Arg Asp Ser Cys Trp Glu Arg Pro Pro Ile Pro Leu
65                  70                  75                  80

Leu Leu Pro Ser Leu Ser Gly Asp Tyr Glu Thr Val Arg Asn Gly Gly
                85                  90                  95

Leu Ile Phe Ala Gly Leu Ala Phe Ile Val Gly Leu Leu Ile Leu Leu
            100                 105                 110

Ser Lys Trp Gly Gly Leu Gln Gly Arg Gly Ala Asp Gln Gly Thr Ser
            115                 120                 125

Leu Leu Lys Ala Ala Glu Gln Ala Gly Phe Arg Glu Leu Pro Arg Glu
    130                 135                 140

Gly
145

<210> SEQ ID NO 9
<211> LENGTH: 15
<212> TYPE: PRT
<213> ORGANISM: Artificial
<220> FEATURE:
<223> OTHER INFORMATION: To raise antibodies against XLas

<400> SEQUENCE: 9

Pro Ala Glu Glu Met Glu Thr Glu Pro Pro His Asn Glu Pro Ile
1               5                   10                  15

<210> SEQ ID NO 10
<211> LENGTH: 15
<212> TYPE: PRT
<213> ORGANISM: Artificial
<220> FEATURE:
<223> OTHER INFORMATION: To raise antibodies against Alex

<400> SEQUENCE: 10

Arg Arg Glu Glu Lys Tyr Pro Leu Arg Gly Thr Asp Pro Leu Pro
1               5                   10                  15
```

PLASMA MEMBRANE BIOMARKERS PREFERENTIALLY EXPRESSED IN PANCREATIC BETA CELLS USEFUL IN IMAGING OR TARGETING BETA CELLS

CROSS-REFERENCE TO RELATED PATENT APPLICATION(S)

This patent application is the national phase entry of PCT/EP2009/051721, filed Feb. 13, 2009, and published, in English, as PCT International Publication WO 2009/101181 A2, on Aug. 20, 2009, and claims priority under Article 8 of the Patent Cooperation Treaty and under 35 U.S.C. §119(e) to U.S. provisional patent application No. 61/066,068, filed Feb. 14, 2008.

STATEMENT OF GOVERNMENT INTEREST

This work was supported by the US Juvenile Diabetes Research Foundation Grant JDRF-4-2001-43. The Juvenile Diabetes Research Foundation may have certain rights in this invention.

FIELD OF THE INVENTION

The present invention is directed to the medical field, in particular to the imaging and quantification of pancreatic beta cell mass, targeting or visualization of pancreatic beta cells for pathology and/or diagnosis of diabetic disorders, follow up of islet transplantation and to purification strategies of pancreatic beta cells.

BACKGROUND OF THE INVENTION

The current global prevalence of diabetes mellitus is approximately 170 million affected individuals and recent projections suggest this will increase to 300 million worldwide by 2025. More than 30 million individuals are affected in Europe. The majority (around 85%) of patients have type 2 diabetes mellitus (T2D), while some 10-15% of the patients suffer from type 1 diabetes mellitus (T1D). Diabetes causes severe long-term complications and psychosocial problems, imposing a heavy burden of morbidity and premature mortality. Diabetes is the leading cause of blindness and visual disability, limb amputation, end-stage renal failure and neuropathy. It is associated with a greatly increased incidence of cardiovascular disease, including stroke, myocardial infarction and heart failure. Cardiovascular disease accounts for more than 50% of all deaths among diabetic patients in Europe. Because T2D is increasingly prevalent and developing earlier in life, increasing the duration of the disease by decades, many more people are developing severe diabetic complications, and suffering decreases their life quality and expectancy.

Diabetes incurs many costs, and is particularly expensive because it is life-long and causes major medical problems. These costs include direct costs from physician and nursing services, hospital services, laboratory services, drugs, education and training of the patients and indirect costs from time lost from work, chronic nursing and general socio-economic support, early retirement, protracted morbidity and premature mortality.

Overall costs of diabetes mellitus, comprising both direct and indirect costs, have been calculated in various countries and are enormous. For instance, the cost of treating one patient over a 25-year period is in the range of 100,000-200,000 EURO. The present invention, by improving early detection and aiding in the development of novel therapies to prevent and/or revert diabetes, will fulfill an enormous unmet need, opening excellent opportunities for the health care industry and for companies involved in medical imaging, production and distribution of tracers for imaging.

The pancreas, an organ about the size of a hand, is located behind the lower part of the stomach. It comprises two structures that are both morphologically and physiologically different: the exocrine pancreas, which produces the enzymes involved in digestion (amylase, lipase, etc.) and sodium bicarbonate and the endocrine pancreas, which produces the hormones involved in the control of blood glucose (insulin, glucagon, somatostatin and pancreatic polypeptide). The cells of the endocrine pancreas are organized as micro-organs dispersed in the pancreas in the form of islets (islets of Langerhans or pancreatic islets). Each pancreatic islet is made up of 4 cell types: alpha cells, beta cells, delta cells and PP cells. The alpha cells are located at the periphery of the islet and secrete glucagon. The beta cells are found at the center of the islet and are the only cells capable of secreting insulin in response to glucose. The delta cells are at the periphery and secrete somatostatin. The function of the PP cells is more controversial (synthesis of pancreatic polypeptide).

Insulin is a hormone that helps the body use glucose for energy. Diabetes develops when the body doesn't make enough insulin, cannot use insulin properly, or both, causing glucose to build up in the blood. In type 1 diabetes mellitus (T1D)—an autoimmune disease—the beta cells of the pancreas no longer make insulin because the body's immune system has attacked and destroyed them. A person who has T1D must take insulin daily to live. Type 2 diabetes mellitus (T2D) usually begins with a condition called insulin resistance, in which the body has difficulty using insulin effectively. Over time, insulin production declines as well, so many people with T2D eventually need to take insulin.

In addition, a condition called hyperinsulinemia occurs in patients with increased beta cell populations when compared to healthy subjects. Patients with hyperinsulinemia are at high risk of developing seizures, mental retardation, and permanent brain damage. Since glucose is the primary substrate used by the CNS, unrecognized or poorly controlled hypoglycemia may lead to persistent severe neurologic damage. Transient hyperinsulinemia is relatively common in neonates. An infant of a diabetic mother, an infant who is small or large for gestational age, or any infant who has experienced severe stress may have high insulin concentrations. In contrast, congenital hyperinsulinemia is rare.

Among the treatments for diabetes, besides the regular administration of insulin, one of the approaches for the physiological control of glycemia and for normalization of glycemia in diabetics is to restore insulin secretion in vivo from cells. Several strategies have been proposed: xenotransplantation of insulin-producing cells from animals, in vitro differentiation of isolated stem cells into insulin-secreting cells and re-implantation thereof in the patient or allotransplantation of isolated pancreatic islets from another subject.

The lack of a cellular model for studying the beta cells, and also the lack of reliable and effective means of cell sorting suitable for this type of cells hinder the study of beta cell functioning and therefore the development of novel methods of treatment of type I and II diabetes.

The current attempts of imaging pancreatic beta cell mass are being done either by using MRI (magnetic resonance imaging) or by using PET (positron emission tomography) and SPECT (single photon emission computed tomography). In vivo imaging of beta cell mass needs a combination of very high sensitivity and high spatial resolution. MRI has the best spatial resolution but its major problem is the ex-vivo labeling procedure and its semi-quantitative nature. MRI has been successfully used by labeling of human islets with SPIO (small particles of iron oxide) ex vivo and subsequent islet transplantation (Evgenov et al 2006). Using this approach, it was possible to follow up the grafted beta cell mass up to 6 months after transplantation. This technique is, however, only usable for transplantation since it relies on ex vivo uptake of the marker by islet cells and can not be used for in vivo imaging of beta cells in the pancreas. MRI was also used for tracking recruitment of diabetogenic CD8+ T-cells into the pancreas (Moore A et al, 2004), for detecting apoptosis in T1D progression using a Cy5.5 labeled annexin 5 probe (Medarova Z. et al, 2006) or for detection of micro vascular changes in T1D progression (Medarova Z. et al 2007), but the changes detected are semi-quantitative.

PET and SPECT have very high sensitivity and do not require ex-vivo labeling. On the other hand, these techniques have a lower spatial resolution as compared to MRI. PET or SPECT imaging is achieved using islet-specific receptor binding compounds or using compounds taken up specifically by transporters in the pancreatic islets labeled with radioactive tracers. Almost all current substrates used for beta cell PET/SPECT imaging bind or are taken up by the non beta cells and, in some cases, even by exocrine cells in the pancreas. This results in dilution of tracer and high backgrounds, making it currently impossible to quantify the beta cells which are scattered over the pancreas in tiny islets (100-300 μm diameter) constituting only 1-2% of the total pancreas mass. This indicates the urgent need of identification of beta cell specific plasma membrane proteins which can be used for imaging or targeting.

The team of Paul Harris identified 35 islet tissue-restricted transmembrane and membrane-associated molecules by comparing microarray datasets obtained in human islets versus exocrine cells (Maffei et al 2004). One candidate, vesicular monoamine transporter 2 (VMAT2), was selected for additional studies on imaging pancreatic beta cell mass using the specific ligand DTBZ. It was recently shown, however, that total eradication of beta cells still resulted in VMAT2 binding, showing that DTBZ is not a good biomarker for imaging pancreatic beta cell mass (Kung et al 2007).

One of few beta-cell specific membrane proteins identified up to now is the zinc transporter ZnT8 or SLC30A8 (Chimienti F et al 2004, Seve et al 2004). ZnT8 co-localizes with insulin in the pancreatic beta cells (Chimienti et al 2006). Avalon (EP1513951 and WO03097802) and CEA (patent US2006246442, EP1563071 and WO2004046355) introduced patents on the fact that this protein was beta cell specific and on the usage of an antibody against SLC30A8 or ZnT8 for cancer therapy and for use in antibody test.

Recently SLC30A8 was identified as an autoantigen and the target of autoantibodies in type 1 diabetes (Wenzlau J M et al., 2007) and it is therefore not useful for beta cell detection.

The company Biogen-IDEC identified Kirrel 2 (filtrin or NEPH3) an immunoglobulin superfamily gene which is specifically expressed in the beta cells of pancreatic islet cells (Sun C. et al, 2003) and in kidney (Rinta-Valkama J et al 2007). Due to its very low expression levels this candidate is not useful for beta cell detection. Recently it was shown that densin and filtrin can act as auto-antigens and auto-antibodies against these are detected in T1D patients (Rinta-Valkama J et al 2007). However, this candidate was too low expressed to be of use in beta cell detection.

Tmem27 or collectrin was identified as a beta cell protein that stimulates beta cell proliferation (Fukui K et al, 2005) and which is cleaved and shed from the plasma membrane. It was not retained in our biomarker list since its expression is higher in the islet non beta cells than in the beta cells.

The free fatty acid receptor GPR40 (also called FFAR1) is a G-coupled receptor recently identified as islet specific and as a possible target for treatment of T2D (Bartoov-Shifman R et al 2007). It was recently suggested to be a possible candidate biomarker for imaging pancreatic beta cells. This receptor, however, is expressed both in islet beta cells and in alpha cells (Flodgren E et al 2007), hampering its potential as a good beta cell biomarker.

The fatty acid receptor GPR119 was identified as a beta-cell specific receptor (Frederiksson R et al, 2003, Chu et al 2007) and oleoylethanolamide (OEA)/lysophosphatidylcholine (LPC)-activated GPR119 is involved in glucose induced insulin secretion. Whether or not these metabolite receptors reach sufficiently high concentrations on the outer surface of the plasma membrane to image the beta cell mass needs to be determined (Madiraju S R et al 2007). GPR119 was identified recently in islet non beta cells (Sakamoto Y et al, 2006) and the selective small-molecule GPR119 agonist PSN632408 suppressed food intake, reduced body weight gain and white adipose tissue deposition (Overton H A et al, 2006) showing that GPR119 is expressed in other tissues.

A random phage-displayed 20-mer peptide library was screened on freshly isolated rat islets but none of the selected peptides were selectively enough in binding to the islets versus other tissues to be used for imaging (Samli K N et al 2005).

PET imaging teams working on pancreas are also attempting to image beta cells. For this purpose, they are using compounds assumed to selectively bind or being taken up by islet-specific transporters and receptors. Examples of these compounds include glibenclamide, tolbutamide, serotonin, L-DOPA, dopamine, nicotinamide, fluorodeoxyglucose, and fluorodithizone. Glibenclamide and fluorodithizone are not specific enough to attain the robust signal to background ratio needed for quantification of beta cell mass via PET imaging. F-deoxy glucose (FDG) could not be used to successfully quantify beta cell mass (Malaisse W J et al. 2000, Ruf J et al. 2006, Nakajo M. et al., 2007) but could be used to discriminate between focal and diffuse hyperinsulinism (de Lonlay P et al 2005 and 2006, Otonkoski T et al 2006, Kauhanen S et al 2007, Ribeiro M J et al, 2007, Hardy O T., et al 2007).

The most promising compounds used up to now to image pancreatic beta cells are F18-DOPA and Dihydrotetrabenazine (DTBZ), both substrates taken up by the VMAT2 transporter (Souza F. et al 2006, Simpson N R. et al. 2006) and Glucagon-like peptide 1 (GLP-1) or exendin (ligands binding to the GLP-1 receptor (Gotthardt M. et al, 2002, Wild M. et al. 2006). Unfortunately, all the compounds mentioned above result in too high background levels and non-specific binding to various other intra-abdominal tissues such as kidney and liver.

As described above, the team of Paul Harris identified vesicular monoamine transporter 2 (VMAT2) and its ligand DTBZ as potential tools for beta cell imaging. DTBZ was labeled with C-11 and F-18 and a high pancreatic uptake was obtained in rodents and primates (Souza et al, 2006). Unfortunately, complete eradication of beta cells reduced the pancreatic uptake of DTBZ by only 30-40% showing that the compound lacks sufficient specificity for the beta cells (Kung et al 2007) to enable its use to assess beta cell mass.

Several auto-antibodies directed against insulin (K14D10), sulfatide (102), glutamic acid decarboxylase (GAD) or protein tyrosine phosphatase (IA2) have been identified. The team of Ian Sweet used a beta cell specific antibody (K14D10) and its Fab fragment for imaging/targeting beta cells but the antibody fragment with the best blood clearance failed to preferentially accumulate in the pancreas. The monoclonal antibody IC2 (Brogren C H et al 1986, Buschard K et al 1988), modified with a radioisotope chelator for nuclear imaging, showed highly specific binding and accumulation to beta-cells with virtually no binding to exocrine pancreas or stromal tissues (Moore A et al, 2001). Sulfatide, however, is also expressed in islet cell innervating Schwann cells and other neural tissues, which may hamper its use in beta cell imaging.

Consequently, there is a lack of specific and reliable markers for the beta cells of pancreatic islets of Langerhans and do not allow reliable beta cell mass quantification. One of the aims of the present invention is to provide such markers.

Our candidates are specific for beta cells and can be used for beta cell specific targeting and non-invasive imaging. They are not induced by inflammation and are not expressed in pancreas surrounding tissues. The use of targeting strategies against these biomarkers will allow early identification of loss in beta cell mass and the follow up of therapies for diabetes, including islet transplantation, attempts at beta cell regeneration etc.

SUMMARY OF THE INVENTION

The present invention is directed to a group of biomarkers located in the plasma membrane of pancreatic beta cells. They were selected by a Systems Biology approach on Massively Parallel Signal Sequencing datasets obtained in human islets and Affymetrix microarray datasets on human islets, purified rat primary beta and non beta cells and insulinoma cells. Based on a set of specific features these biomarkers are unique candidates for imaging and targeting strategies to study the pancreatic beta cell mass in health and disease (T1D, T2D, pancreatic cancers or islet transplantation).

The five specific features of the selected biomarkers are:
1) Preferentially expressed in pancreatic islets as compared to surrounding tissues (total pancreas/exocrine tissue, liver, intestine, spleen, stomach)
2) Higher expression in pancreatic beta cells than in pancreatic alpha cells or than in other islet non-beta cells
3) Expression levels in pancreatic beta cells are higher or comparable to glucokinase which is an enzyme specifically expressed in the pancreatic beta cell
4) Located in the membrane and as such targetable with antibodies, peptides or small molecules which allows imaging, targeting and immunohistochemistry
5) Expression is not induced during the process of inflammation of the beta cell mass and the protein is not enriched in T-cells and dendritic cells or in other cells participating in the inflammation process.

Imaging/targeting strategies using labeled antibodies, aptamers, interacting proteins or ligands directed against these biomarkers will allow beta cell specific mass quantification, evaluate the progression of diabetes/pancreatic cancer and will lead to earlier prediction of pancreatic disease state, allow earlier intervention and higher chance to cure or halt diabetes, and enable the follow up of beta cell mass following islet transplantation.

The biomarkers of the invention can also be potential targets for autoimmunity in T1D, as is the case of other abundant beta cell surface proteins, and may thus be a target for auto-antibodies. Detection of these auto-antibodies may allow prediction of T1D.

Another application of the biomarkers of the invention will be the follow up of beta cell mass in patients with type 1 and type 2 diabetes and following islet transplantation. Beta cell imaging will be also useful as a surrogate marker for clinical trials of new therapies aiming to prevent beta cell mass loss in diabetes or to restore beta cell mass by regeneration. The biomarkers could also be targeted to deliver agents to stop inflammation in the case of T1D or transplantation.

The invention therefore provides for the use of a marker selected from the group consisting of FXYD2-gamma-a, FXYD2-gamma-b and FXYD2-gamma-c, for specifically measuring pancreatic beta cell mass. In a preferred embodiment, said marker is FXYD2-gamma-a.

In an alternative embodiment, the invention provides a method for measuring pancreatic beta-cell mass comprising the steps of:
a) visualizing the beta cells in a sample using a labelled molecule specifically binding to one or more FXYD2-gamma isoform(s) such as FXYD2-gamma-a, FXYD2-gamma-b and/or FXYD2-gamma-c,
b) quantifying the amount of labelled beta cells.

In a preferred embodiment, said marker is FXYD2-gamma-a.

In a further embodiment, use of a binding molecule specifically binding to one or more FXYD2-gamma isoform(s) such as FXYD2-gamma-a, FXYD2-gamma-b and/or FXYD2-gamma-c in the preparation of a diagnostic composition for the in-vivo diagnosis of pancreatic beta-cell related disorders. In a preferred embodiment, said marker is FXYD2-gamma-a.

In another embodiment, the invention provides for a method of in vivo diagnosing a beta-cell-related disorder encompassing the following steps:
a) introducing an isotopically labelled tracer molecule, specifically binding to one of the markers selected from the group consisting of FXYD2-gamma-a, FXYD2-gamma-b and FXYD2-gamma-c, into a subject,
b) visualizing the tracer molecule specifically located to the beta cell population in the pancreas using PET, PET-CT or SPECT in vivo,
c) quantifying the beta cells mass in said subject,
d) comparing of the beta cell mass data obtained in step c) with the beta cell mass of a healthy subject,
e) diagnosing the subject as having diabetes or being at risk of having diabetes when the level of beta cell mass obtained in step c) is reduced as compared to that of a healthy subject and diagnosing the subject as having hyperinsulinemia or being at risk of having hyperinsulinemia when the level of beta cell mass obtained in step c) is increased as compared to that of a healthy subject. In a preferred embodiment, said marker is FXYD2-gamma-a.

Preferably the beta-cell-related disorder analyzed in any of the methods of the invention is type 1 diabetes mellitus, type 2 diabetes mellitus, hyperinsulinemia or pancreatic cancer.

Alternatively, the invention further provides for a kit for specifically measuring beta cell-mass and/or for diagnosing a beta-cell-related disorder and/or for purifying beta cells in a subject comprising:
a) a labelled molecule binding to any one of the biomarkers selected from the group consisting of FXYD2-gamma-a, FXYD2-gamma-b and FXYD2-gamma-c. In a preferred embodiment, said marker is FXYD2-gamma-a.

In any of the methods of the invention, the binding molecule preferably is a specific antibody, antibody fragment, nanobody, affybody, an aptamer, a photoaptamer, a small molecule, an interacting partner, a specifically binding protein or peptide, a Darpin, an ankyrin, an isotopically labelled tracer or a ligand, specifically binding to said biomarker.

In a preferred embodiment, the antibody is directed against the FXYD2-gamma-a, -b or -c biomarker, even more preferably the antibody is directed to any one of the peptides of SEQ ID NO: 1-5, preferably of SEQ ID NO: 1-3, more preferably of SEQ ID NO:1.

The invention further provides for a method for following up the success of the transplantation of beta cells in a subject comprising the following steps:

a) measuring the amount of beta-cell mass in the subject in a certain period of time after transplantation of the subject with pancreatic islets.

b) determining the success of the islet transplantation by comparing the beta cell mass in the course of time Alternatively, the invention provides for a method for purifying or isolating beta cells from other pancreatic non-beta cells comprising the following steps:

a) tagging the beta cells with a labelled binding molecule specifically directed to one of the markers selected from the group consisting of FXYD2-gamma-a, FXYD2-gamma-b and FXYD2-gamma-c, b) isolating the labelled cells from the non-labelled cells through the tag on the beta cells, thereby obtaining a substantially pure beta cell preparation. In a preferred embodiment, said marker is FXYD2-gamma-a.

In a further embodiment, the invention provides for a method for identification of regeneration of beta cells comprising the steps of:

a) tagging the beta cells with a labelled binding molecule specifically directed to one of the markers selected from the group consisting of FXYD2-gamma-a, FXYD2-gamma-b and FXYD2-gamma-c, b) isolating the labelled cells from the non-labelled cells through the tag on the beta cells, thereby obtaining a substantially pure regenerated beta cell preparation c) performing immunohistochemistry to identify the number of newly regenerated beta cells, and to define the new beta cell mass follow up op therapeutic strategies and detect beta cell mass recovery. In a preferred embodiment, said marker is FXYD2-gamma-a.

The tags used in the above methods could be magnetic beads or paramagnetic beads. The beta-cell mass could then be measured using MRI.

Further, the invention provides for a method for identification of stem cell populations in order to derive functional insulin-expressing cells, comprising the steps of:

a) tagging the treated stem cells with a labeled binding molecule specifically directed to one of the markers FXYD2-gamma-a, FXYD2-gamma-b and FXYD2-gamma-c, and b) isolating the labeled cells from the non-labeled cells through the tag on the potential beta stem cells, thereby obtaining a substantially pure beta stem cell preparation. In addition, this method can further comprise the steps of: c) performing immunohistochemistry to identify the number of beta stem cells, and to define the new beta cell mass, and d) follow up op therapeutic strategies and detect newly formed beta cell mass. In a preferred embodiment, said marker is FXYD2-gamma-a.

In another embodiment, the invention also provides for a method for identifying specific biomarkers for pancreatic beta cells comprising the selection of such a marker based on the following 5 criteria:

a) more than 50-100 times enriched in human islets versus total human pancreas, b) enriched in purified rat beta cells compared to purified rat non beta cells making them relatively beta cell specific, c) expressed at a level similar or higher than glucokinase, d) located in the plasma membrane and can be used for targeting with specific antibodies or with peptides, and e) expression level of the selected genes/proteins is not modified during inflammation.

Preferably, the expression data obtained is derived through MPSS and/or gene expression (mRNA) microarray technology.

In addition, the invention also provides new markers identified by the methods of the invention such as: FXYD2-gamma-a, FXYD2-gamma-b and FXYD2-gamma-c. In a preferred embodiment, said marker is FXYD2-gamma-a.

Finally, the invention also provides for the use of one or more markers selected from the group consisting of: GNAS-XLas, GNAS-Alex, CDIPT, VAT1, CLSTN1, SLC7A5, CTTN, BAIAP3, LYPD1, ANXA7, DMBT1, KIAA1543 and SLC7A8, for specifically measuring pancreatic beta cell mass or for use in any one of the methods, kits and uses as described in the present invention, wherein the FXYD2-gamma marker(s) can be replaced by any one or more other marker(s) of said group of markers, or wherein any one or more of the markers of said list can be used in combination with the FXYD2-gamma marker(s).

BRIEF DESCRIPTION OF THE DRAWINGS

FIG. 1: Members of the FXYD family. Underlined fragments refer to signaling peptides. Note the FXYD conserved region depicted in bold.

FIG. 2A: N-terminal sequence of the FXYD2 gamma a and b splice variants in different species.

FIG. 2B: Alignment of the amino acid sequence of the three splice forms of human FXYD2-gamma, isoforms a, b and c.

FIG. 7: FXYD2-gamma-a and FXYD2-gamma-b are selectively expressed in human pancreatic islets, while expression is absent in insulinoma. Human normal pancreas sections were analysed by immunohistochemistry with a monoclonal antibody directed against FXYD2 (Abnova) (A. and B. magnifications 200× and 400×, respectively) and with the polyclonal anti-FXYD2-gamma-a (SPY393) (C. and D.

magnifications of 200× en 400× respectively). Consecutive sections of insulinoma (magnification 100×) were analysed with anti-insulin antibody (E) and SPY393 (F).islets.

Figure 8A:
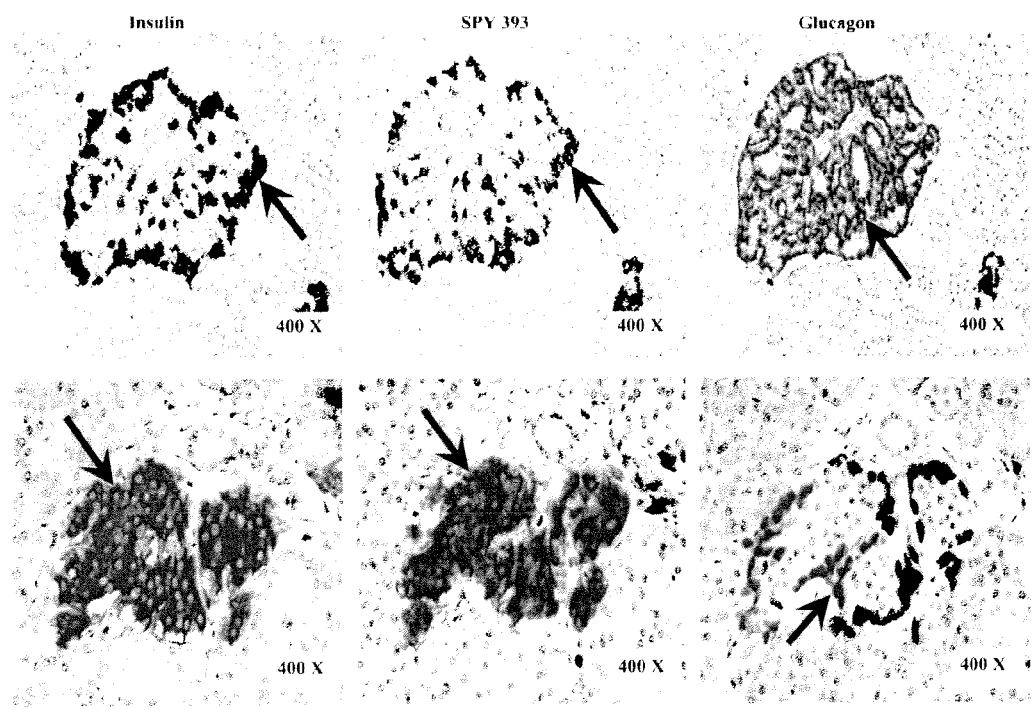
Figure 8B:
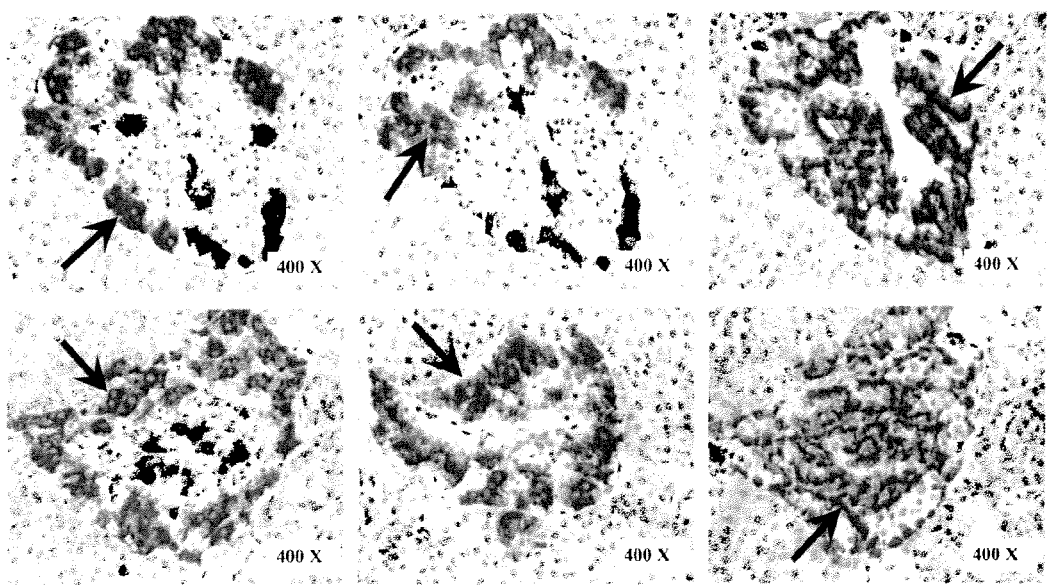

FIGS. 8 (a and b): FXYD2 expression is restricted to the human pancreatic beta cells. Consecutive sections of 3 μm were taken and stained with anti-insulin antibody, SPY393 antibody (anti-FXYD2 gamma a) or anti-glucagon antibody. The 2 panels show 2 independent experiments each experiment showing 2 different islets: localization of FXYD2 and insulin is similar.

FIG. 9: Human pancreas sections were analysed by immunofluorescence. Upper panel: Sections were incubated with the SPY393 antibody and anti-rabbit IgG-TRITC labelled (red) together with a monoclonal antibody against glucagon (K79bB10, Sigma) and an anti-mouse IgG-FITC labeled (green). No colocalisation is seen between FXYD2 expressing cells (red) and glucagon expressing α-cells (green). Lower panel: Sections were incubated with the SPY393 antibody and anti-rabbit IgG-TRITC labeled (red) in combination with a monoclonal antibody against insulin (K36aC10, DBS) and an anti-mouse IgG-FITC labeled (green). A very good co-localization (orange staining) is seen between FXYD2 expressing cells (red) and insulin-expressing β-cells (green). Quantification of the colocalisation is shown in Tables 4 and 5 below.

Figure 10:
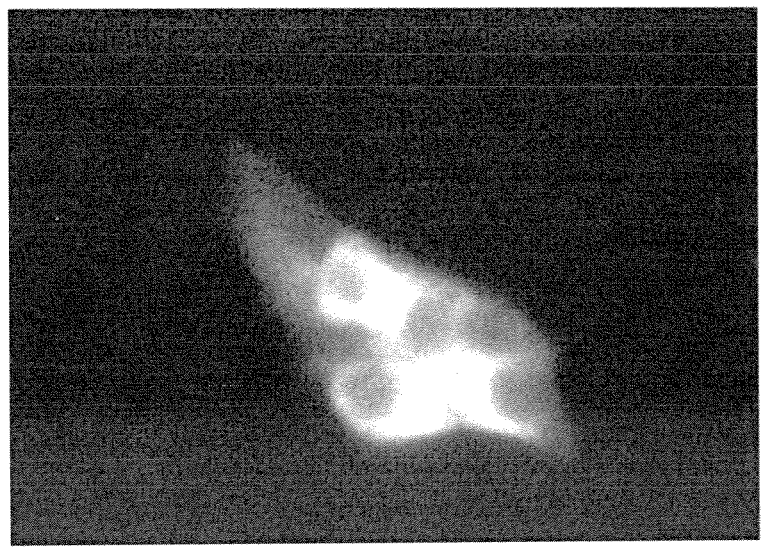

FIG. 10: FXYD2 expression in rat dispersed islet cells: FXYD2 is detected both in the cytoplasm and on the membrane of the islet cells. Rat dispersed islet cells were fixed on polylysine coated glass slides and incubated for 2 days to recover from the isolation procedure. The cells were then fixed with 4% paraformaldehyde and treated with 0.3% TX100 and blocking was performed with normal goat serum. Immunocytochemistry was performed with the SPY393 detecting FXYD2 gamma-a and with a second anti-rabbit antibody labelled with ALEXA. Nuclei (in grey see arrow) are FXYD2 negative, FXYD2 (shown as bright) is seen both in cytoplasm and membrane.

Figure 11:
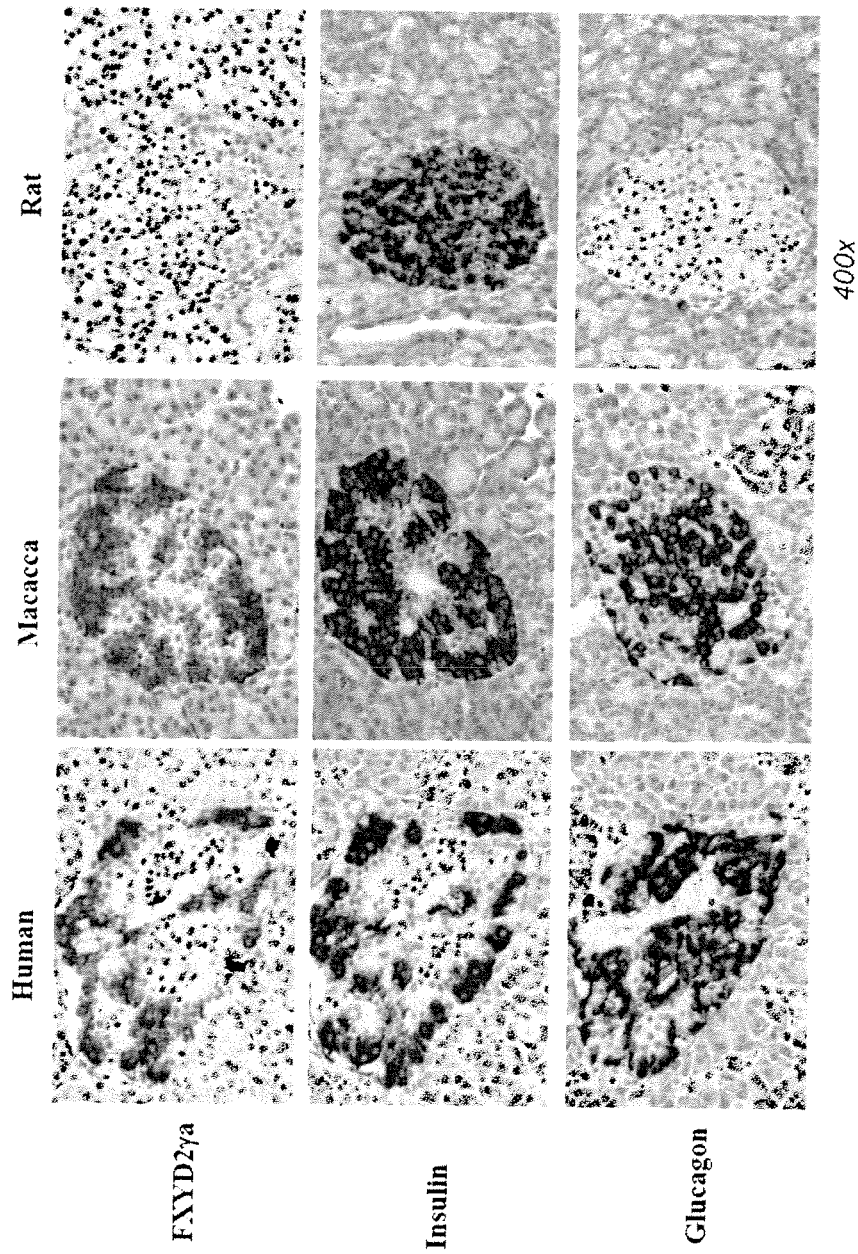

FIG. 11: FXYD2-gamma-a is specifically expressed in beta-cells in human, Macaca mulatta and rat pancreas. Consecutive paraffin sections of human (left column), Macaca mulatta (middle column) and rat (right column) pancreas were analysed by immunohistochemistry with polyclonal rabbit anti-FXYD2-gamma-a (SPY393) (upper row), anti-insulin antibody (middle row) or anti-glucagon antibody (lower row) (magnification 400×).

Figure 12:
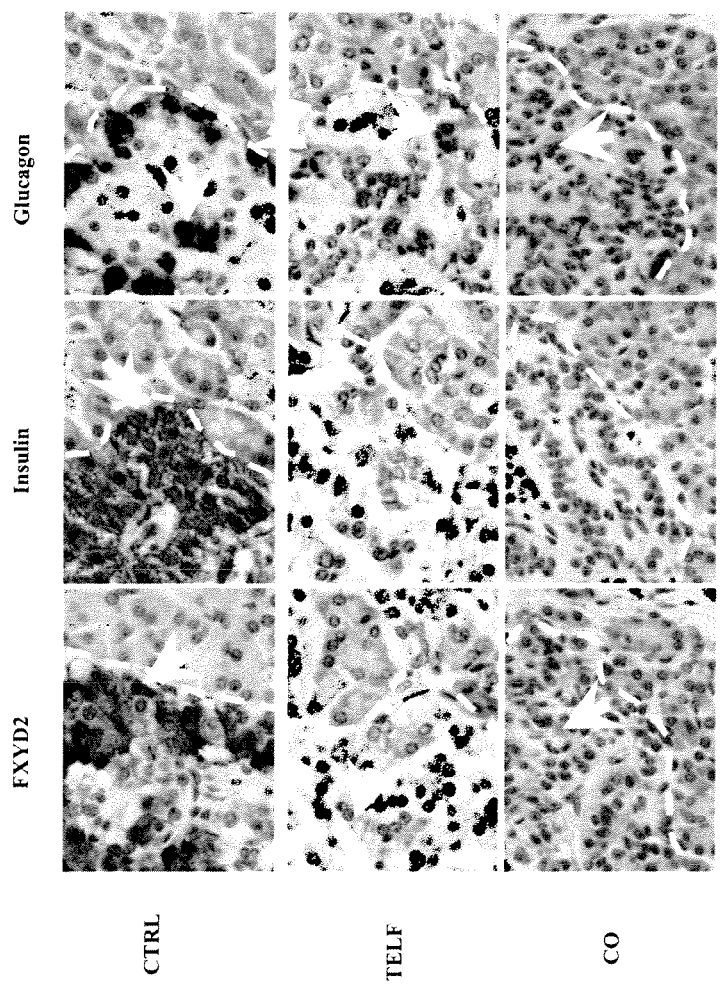

FIG. 12: Expression of FXYD2-gamma-a is drastically decreased in islets from type 1 diabetes patients (CO and TELF; these codes identify two patients, deceased respectively 3 days and 5 years after the diagnosis of type 1 diabetes) compared to normal pancreas (CTRL). Consecutive sections of 3 μm were taken and stained with SPY393 antibody, anti-insulin antibody or anti-glucagon antibody. In the TELF pancreas, beta cells can not be detected based on insulin staining; this was correlated with disappearance of FXYD2 staining. In the CO pancreas, beta cells can not be detected based on insulin staining but a very faint staining of FXYD2 remained (magnification 1000×).

Figure 13:
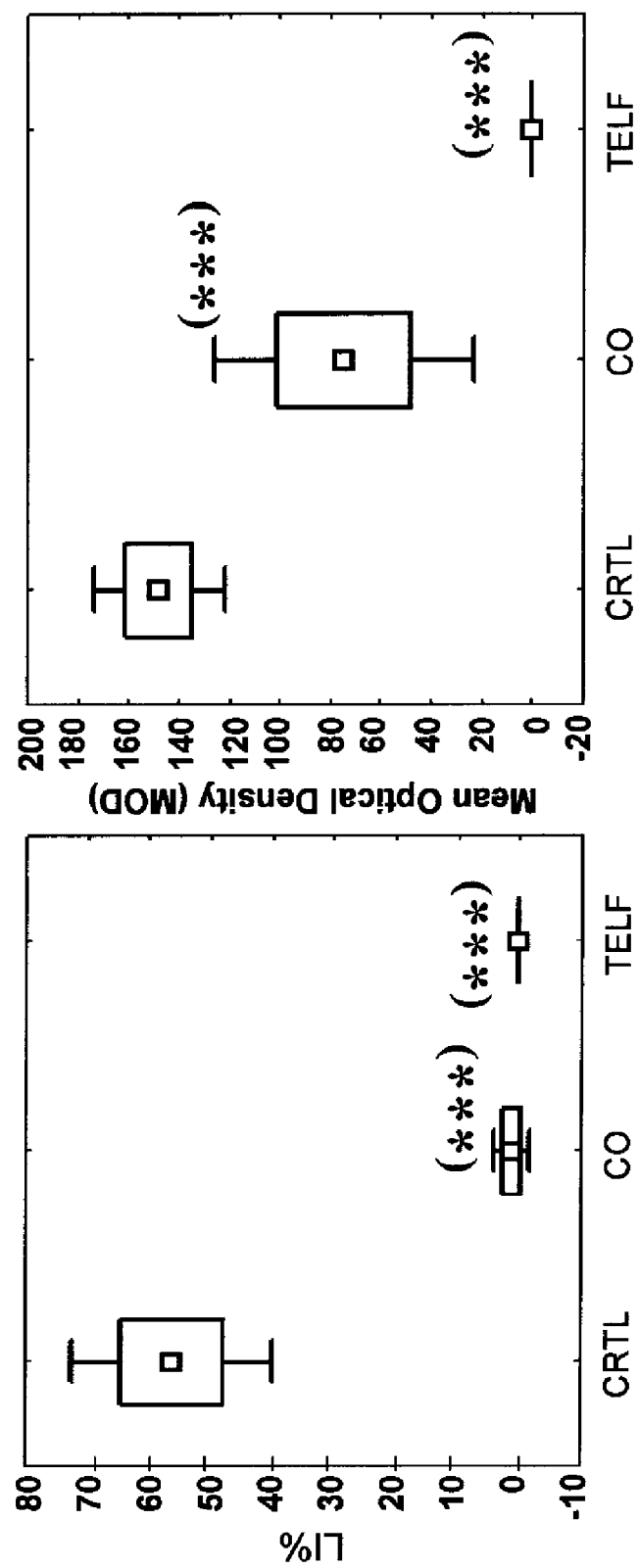

FIG. 13: Quantification of the FXYD2-gamma-a in islets from type 1 diabetes patients: 20 Langerhans islets/case were quantified; % of stained tissue area (Labelling Index—LI) and mean staining intensity. As seen in the FIG. 14 above: in the TELF pancreas: FXYD2 staining completely disappeared and this correlated with the disappearance of beta cells as identified by insulin staining. In the CO pancreas staining for insulin disappeared and this correlated with a 50 fold decreased staining for FXYD2-gamma-a when comparing the labeling index (LI) with CTRL.

Figure 14:
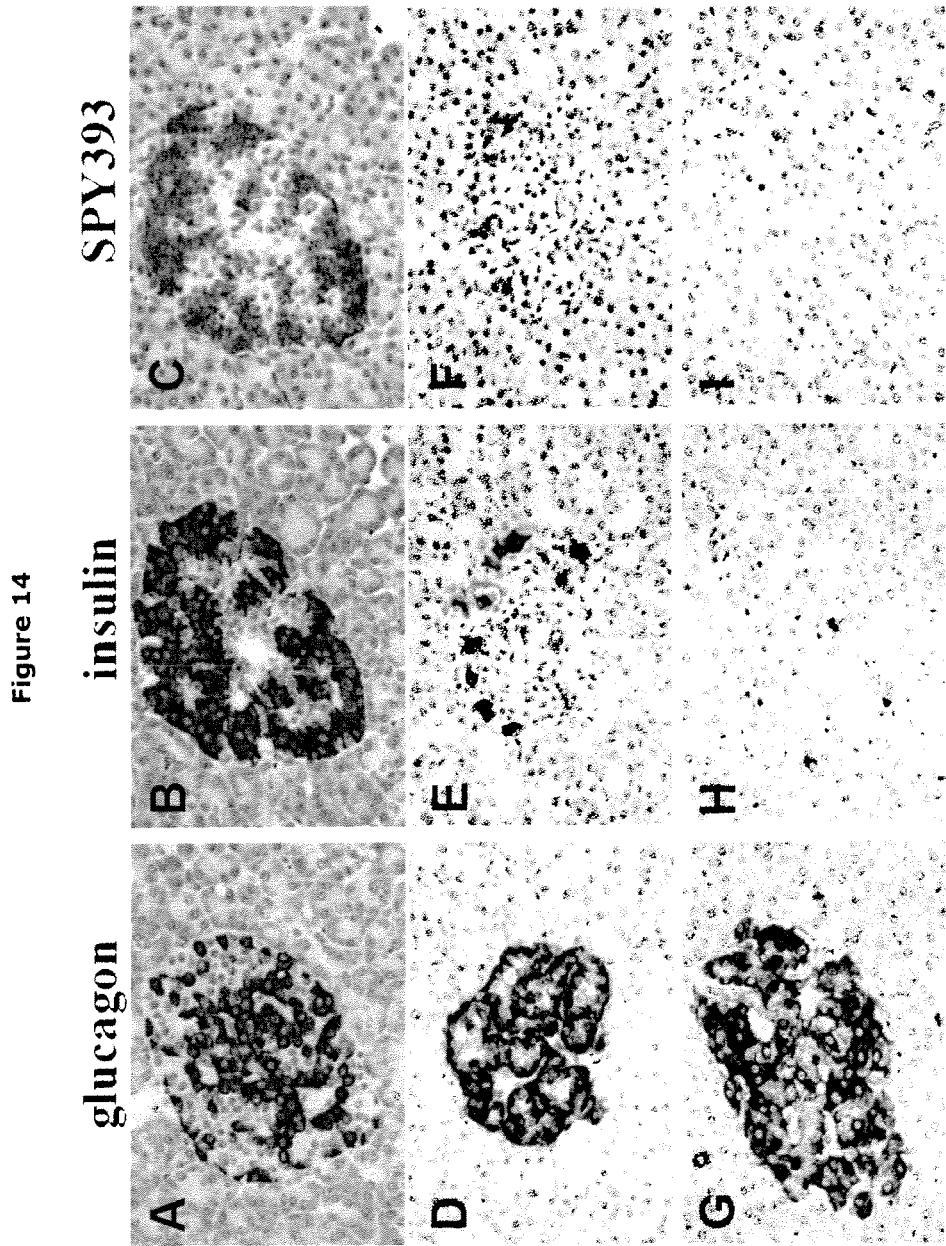

FIG. 14: Decreased FXYD2-gamma-a expression correlates with beta-cell loss in STZ-treated Macaca mulatta. Consecutive sections of pancreas from control (A-C, CT) and STZ-treated Macaca mulatta (D-F, primate 1 and G-I, primate 2) were analysed with anti-glucagon antibody (left column A, D, G), anti-insulin antibody (middle column B, E, H) or SPY393 polyclonal anti-FXYD2-gamma-a (right column C, F, I). Magnification 400×.

Figure 15:
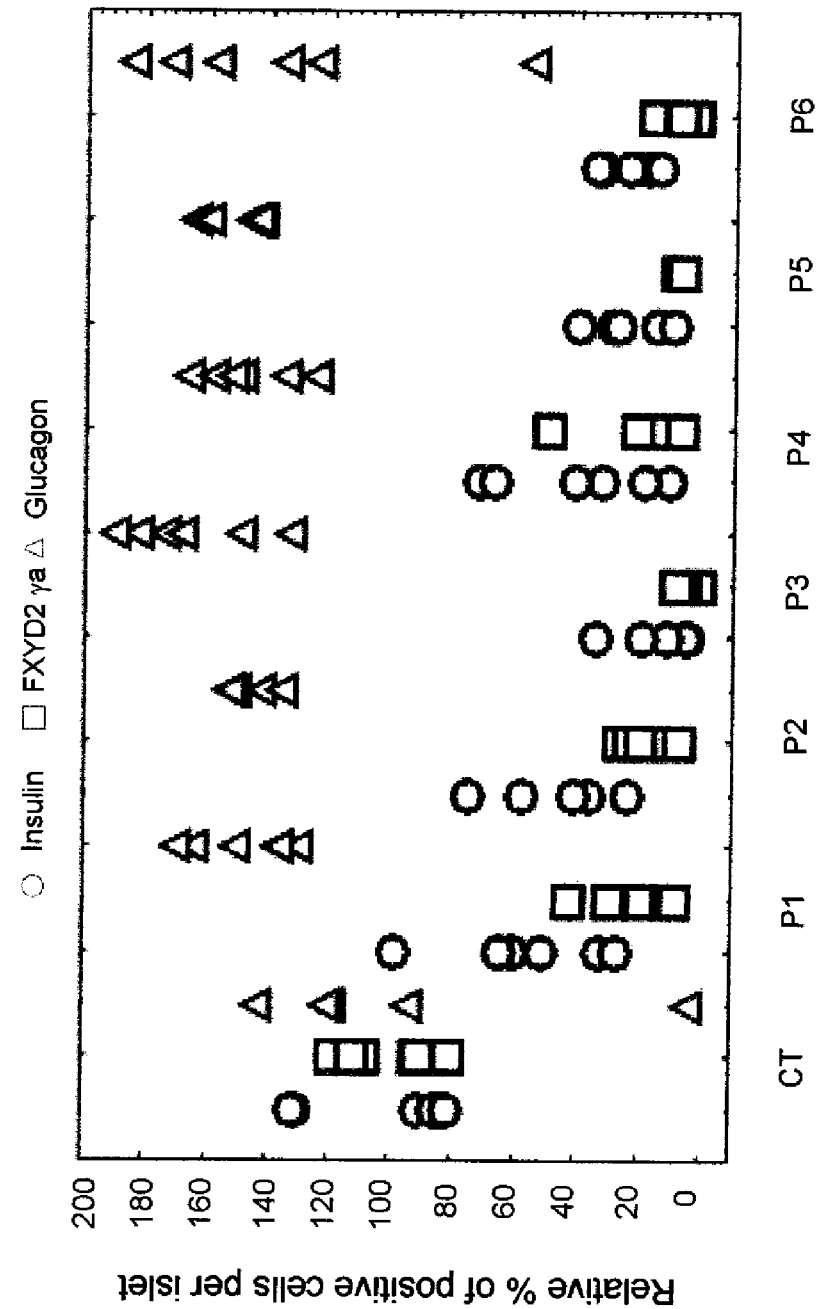

FIG. 15: Significant decrease in insulin and FXYD2-gamma-a expression in the pancreas of STZ-induced diabetic Macaca mulatta.

Pancreas sections from control (CT) and STZ-induced diabetic Macaca mulatta (Primate P1-6) were analysed. Six islets per case were counted by three observers unaware of sample identity. Glucagon positive, insulin positive and FXYD2-gamma-a positive cells were calculated as relative percentage per islet; Values in CT were considered as 100%.

Figure 16:
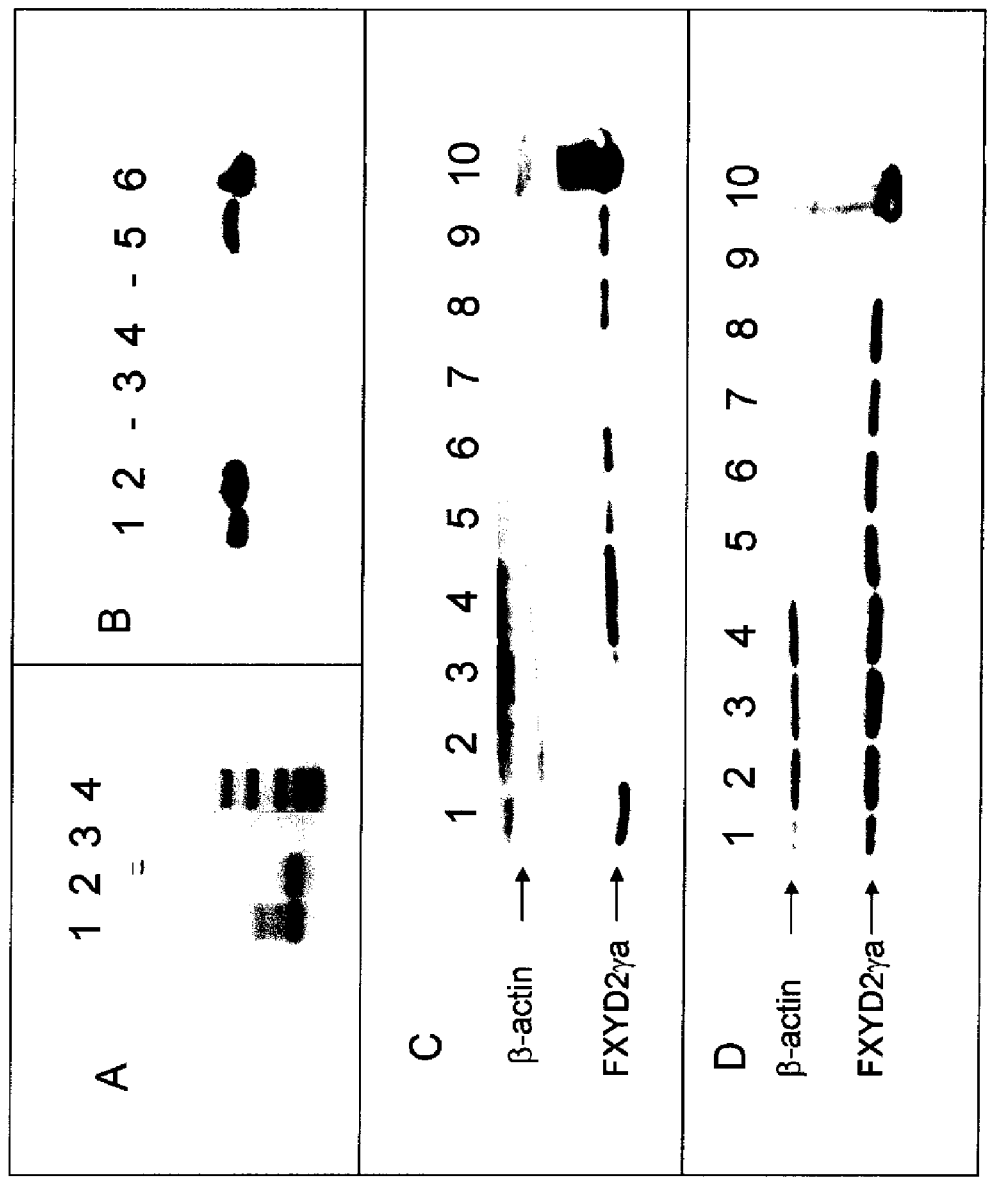

FIG. 16: Expression of FXYD2-gamma-a and -gamma-b isoforms in rodent pancreatic islets, rat INS-1E, AR42J cells and in human CAPAN-2 cells but not in human PANC-1 cells. FXYD2-gamma-a expression is not changed after 24 h exposure to cytokines.

A. FXYD2 gamma-a and gamma-b splice variants were detected in mouse pancreatic islets. Primers were used to detect FXYD2-gamma-a isoform (lane 1), FXYD2-gamma-b isoform (lane 2) and FXYD2-gamma-c isoform (lane 3); Marker (M; lane 4).

B. The polyclonal anti-FXYD2-gamma-a antibody (SPY393) recognizes only the FXYD2-gamma-a isoform. Rat dispersed pancreatic islet cells (lanes 3, 5) and rat kidney (lanes 1, 2, 4, 6) were analysed. Lane 1 SPY393 with FXYD2-gamma-b blocking peptide, lane 2 SPY393 with an aspecific blocking peptide, lane 3 and 4 with SPY393 with FXYD2-gamma-a blocking peptide and lane 5 and 6 with SPY393 without blocking peptide.

C. Western blot analysis was performed on total cellular extracts of CAPAN-2 cells (lane 1), PANC-1 cells (lane 2), AD293 cells (lane 3), INS-1E cells (lane 4) and dispersed rat islets control (lane 5, 8) and exposed to cytokines for 24 h (lane 6, 9), marker (lane 7), rat kidney positive control (lane 10). The lower arrow marks FXYD2-gamma-a expression detected by SPY393, the upper arrow marks beta-actin detected with a polyclonal rabbit anti-beta-actin.

D. Western blot analysis was performed on total cellular extracts of INS1E cells exposed for 24 h in control condition (lane 1), or to IL1beta (lane 2), IL1beta+IFN-gamma (lane 3), IFN-gamma alone (lane 4) and similarly on total cellular extracts of AR42J cells exposed for 24 h in control condition (lane 5), or to IL1 beta (lane 6), IL1beta+IFNgamma (lane 7), IFN-gamma alone (lane 8), marker (lane 9) and rat kidney total cellular extract (lane 10). The lower arrow marks FXYD2-gamma-a expression detected by SPY393, the upper arrow marks beta-actin detected with a polyclonal rabbit anti-beta-actin. The blots are representative of 3-4 independent experiments.

FIG. 17: Biodistribution study in Macaca mulatta.

The animals were injected with SPY393 antibody labeled with $^{124}$I. PET scans were performed at different time points after the injection (hours Post Injection or PI): Panel A: 3 hours PI; B: 24 hours PI; C: analysis of stomach content at 72 hours PI, indicating the tracer molecule is abundantly taken up by the stomach, perturbing visualization in other parts of the body.

Figure 18:
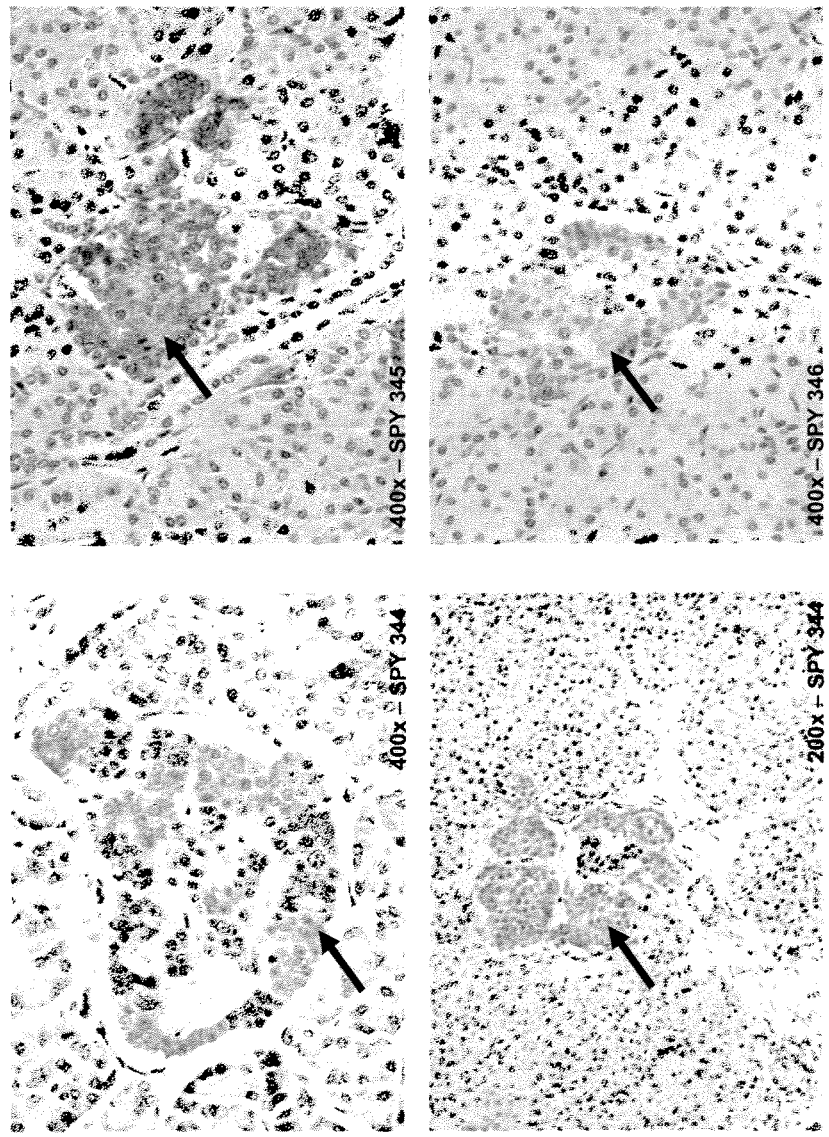

FIG. 18: Rabbit polyclonal antibody SPY344 detect specifically XLas in pancreatic islets in human paraffin pancreas sections (shown in the figures left). Rabbit polyclonal antibody SPY345 detects specifically Alex in pancreatic islets in the human paraffin pancreas sections (shown in the figure right above). SPY346 also specifically detects Alex in pancreatic islets but staining is less intense (Fig B, right below).

DETAILED DESCRIPTION OF THE PREFERRED EMBODIMENTS

The present invention is directed to a group of biomarkers specifically located in the plasma membrane of pancreatic beta cells. They were selected by a Systems Biology approach on Massively Parallel Signal Sequencing datasets obtained in human islets and Affymetrix microarray datasets on human islets, purified rat primary beta and non beta cells and insulinoma cells. Massively parallel signature sequencing (MPSS) generates millions of short signature sequence tags from the 3'-regions of mRNA samples, the majority of which can be unambiguously assigned to individual genes, with the number of tags present for each gene being a digital readout of corresponding mRNA abundance. Because individual cells contain an estimated 200,000-300,000 transcripts, sampling at this level approaches the complete cataloging of all different mRNA species expressed in a cell line or tissue. Comparison of MPSS data sets derived from different tissues provides a powerful means of defining tissue-specific gene expression.

Our selected candidates are not only specific for pancreatic islets versus exocrine tissue but we added a number of extra selection criteria which makes our candidates better for the use as beta cell imaging and targeting. We used unique datasets containing quantitative information (instead of comparative information) to select the biomarkers. The unique features assigned to our selected biomarkers are:

1. Selected biomarker candidates are enriched more than 50-100 times in human islets versus total human pancreas: Instead of using comparative data obtained by micro array, we have quantitative data obtained by MPSS which gives the number of transcripts per million; this allows us to calculate how much a transcript is enriched in human islets versus total human pancreas. Since islets constitute 1-2% of the total pancreas, we used as selection criteria an enrichment of 50-100 times in islets versus pancreas. Using the quantitative data we can calculate how many times the expression will be enriched in human pancreatic islets versus the surrounding human tissues (stomach, spleen, intestine) or versus tissues used for placing islet grafts (liver, kidney) based on comparison with publicly available human MPSS datasets; this is a very useful criteria for anticipating background levels and for selecting islet specific candidates. The enrichment in islets versus total pancreas is preferably higher than 50 fold.

2. Selected candidates are enriched in purified rat beta cells compared to purified rat non beta cells making them relatively beta cell specific. The islet composition changes during the evolution of T1D due to loss of beta cells and the relative increase in non beta cells (mostly alpha cells). It is thus crucial for quantification of beta cell mass that putative biomarkers are specifically expressed in beta cells. The present selection was done based on our unique data set obtained with microarrays performed on purified primary beta cells compared to purified primary non beta cells. Until now no such selection has been done. The term "enriched" means that a higher level of expression is obtained in beta cells when compared to non-beta cells, manipulated under identical conditions. As this analysis is done based on microarray data analysis, the FC change is not taken in account (f.e. some probes for FXYD2 are not so good rat microarray as compared to previous data in human and give here a FC of 1.4; On the other hand some probesets f.e. GNAS probes score very high (comparable to insulin) and there again FC will be 1.3) so we selected genes that were higher expressed in beta cells than in non-beta cells but no FC criteria was set as such.

3. The selected biomarkers are expressed at a level at least as high as, but preferably higher than the expression level of glucokinase. For imaging the targets need to be expressed in sufficient amount on the pancreatic beta cells to enable detection. We have both quantitative data in human islets and comparative data in human islets and primary rat beta cells to check this criterion; this is done by comparison with glucokinase, a moderately expressed enzyme in the beta cells.

4. The selected biomarkers are located in the plasma membrane and can be used for targeting with specific antibodies, chemical synthesis, natural compounds or with peptides. Antibodies and peptides targeting these proteins detect native structures located on the plasma membrane proteins with an affinity high enough to perform imaging/targeting. The localization in the plasma membrane was assessed by a Systems Biology approach (IPA analysis, GO analysis, literature screening) and we perform immunohistochemistry to confirm this localization.

5. The expression level of the selected genes/proteins is not substantially modified (e.g. induced) during inflammation: We have a large amount of microarray data comparing control condition to conditions in which inflammation is induced (e.g. cytokine-treated or virus- or dsRNA-exposed beta cells). During inflammation pancreatic beta cells often express similar markers as those found in immune cells (T-cells, dendritic cells) infiltrating in the pancreas. It is thus of major importance to select biomarkers exclusively expressed in the beta cells and not induced during inflammation in order to quantify beta cell mass. By comparison of our microarray datasets with the publicly available Symatlas we could confirm these data. This analysis was not done previously by other groups. Via literature screening we detected expression in normal human pancreas compared to different types of pancreatic cancer and their expression in NOD mice (T1D mouse model) versus control mice. If not available in literature we checked this in mouse TME specially made to clarify this issue. The term "not substantially modified (e.g. induced)" means that the expression level of the candidate marker is not induced in inflammatory versus non-inflammatory conditions. This is to counter the possible effect of inflammation increasing the expression in an equal amount of decrease in beta cell-mass due to a disease condition such as diabetes. (i.e. if the decrease in beta cell mass in diabetic conditions would be about 30% and the marker as such has an increased expression of about 30% due to inflammation condition, this would not allow to detect changes in beta cell mass based on said marker).

Next, a procedure was developed to analyze the three best candidates of our list at the protein level and to confirm islet- and beta cell-specificity. For the candidates we selected antibodies if available or prepared antibodies specifically targeting the biomarkers. The selected candidates and the antibodies targeting these candidates were tested in human tissue microarrays confirming their specificity for pancreas (versus surrounding tissues) and their specific expression in pancreatic islets versus exocrine tissue. The protein expression of the biomarkers was subsequently validated for its specificity to beta cells versus non beta cells via immunocytochemistry on pancreatic slices of normal and diseased human and rodent pancreas (human pancreatic cancer and T1D mouse model).

With this set of criteria we obtained a unique group of biomarkers selectively expressed on the plasma membrane of human and rodent pancreatic beta cells. The expression level is high enough to perform imaging/targeting and their expression level is not substantially modified by inflammation and diabetic conditions or they have not been previously identified as auto-antigens. This makes them perfect candidates for imaging/targeting of beta cells.

The great advantage of the present invention is to enable determination of pancreatic beta cell mass in diabetes mellitus (see below). Of note, there are presently no other available methods to specifically measure beta cell mass.

Type 1 diabetes (T1D) is an autoimmune disease in which the body's immune system attacks and kills its own insulin-producing beta cells and kills them. A key obstacle to early detection of T1D, to understand the evolution of the disease and to assess the effectiveness of novel therapeutic interventions to prevent the disease is the lack of direct, noninvasive technologies to visualize and measure beta cell mass. The lack of reliable methods to determine beta cell mass also limits follow up of pancreatic islet transplantation and of patients affected by type 2 diabetes (T2D), a disease where a progressive decrease of beta cell mass (albeit of less magnitude than T1D) is also present. To achieve the goal of beta cell imaging, there is an urgent need for beta cell specific membrane proteins which can be visualized. To solve this problem, we have selected candidate beta cell biomarkers by a Systems Biology approach. The results obtained indicate that:

The selected candidates are highly enriched in human pancreatic beta cells. Antibodies, small molecules or peptides directed against them can be made into tracers to be used for PET or MRI or SPECT imaging. These tracers will bind preferentially to beta cells, enabling very good specificity and selectivity. In later stages of T1D, when there is a severe decrease in the number of beta cells and a relative increase in alpha cells, beta cell specific biomarker will allow quantification of the remaining beta cell mass without background from non beta cells. These biomarkers will also allow follow up of pancreatic islet transplants, examination of the progressive decrease in beta cell mass in type 2 diabetic patients or of an eventual increase in beta cell mass in obese non-diabetic patients (in this case, there is an increase in beta cell mass that compensates for the insulin resistance).

The selected biomarkers are not induced by inflammation and will not target infiltrating immune cells. Beta cells express autoantigens which are detected by infiltrating immune cells. Since we compare the expression of our selected biomarkers in control and inflamed beta cells and select membrane proteins which are not expressed in immune cells we will be able to follow the beta cell mass during inflammation (insulitis)

The selected candidates allow non invasive imaging of islet grafts following human islet transplantation and allow adjustment of immunosuppressive therapy to support graft survival and earlier interventions with the aim of rescuing transplants who are under augmented immune assault.

Endogenous antibodies targeting the candidates, arising as part of the autoimmune process in T1D, are valuable markers of autoimmunity and help in the detection of patients at a high risk to develop the disease.

The current agents used for imaging the pancreas include reagents such as glibenclamide, dopamine, fluorodeoxyglucose, fluorodithizone and DOPA. The uptake of these agents in beta cells, as compared to exocrine pancreas and non beta cells in the islets, is not sufficient to allow reliable imaging of beta-cell mass (Sweet et al, 2004).

Our biomarker list was selected from unique datasets containing quantitative expression information in human islets (MPSS) and comparative expression data obtained from microarray datasets obtained in purified primary rat beta cells and primary rat non-beta cells. The biomarkers selected here fit the following criteria:

1. The "islet specific" criteria is based on comparison of quantitative MPSS data from human islets compared to MPSS from 32 human tissues (obtained from the LICR MPSS dataset, publicly available database which includes total pancreas). We selected an enriched expression of more than 50 fold in islets versus pancreas. This is a new feature, since quantitative MPSS datasets on human islets were not previously available.

2. The "beta cell specific", i.e. expressed more in beta cells than in alpha cells. This criteria is important for imaging beta cells in diseased states such as Type 1 Diabetes (T1D). During the evolution of T1D, beta cells progressively disappear while the number of alpha cells increase. It is therefore necessary to have biomarker(s) specific for beta cells and not or lowly expressed in alpha cells.

3. Expression levels should be higher or comparable to glucokinase. Glucokinase is an enzyme highly and selectively expressed in beta cells, and comparison against glucokinase provides a reliable assessment of high expression of the potential biomarker.

4. The present biomarkers are plasma membrane located. We first used the TMHMM program to detect transmembrane regions, which was followed by a thorough literature analysis; GO analysis and Ingenuity pathway analysis were used to complement this criteria.

5. Expression levels are not induced by inflammation. Expression levels of selected biomarkers are not increased in condition of inflammation (exposure to cytokines or virus-induced) in our microarray datasets obtained in human islets and in purified primary rat beta cells. This assures that modifications in the expression of the biomarker during insulitis, prevailing in early T1D, will not introduce spurious assessment of beta cell mass.

In conclusion, the biomarkers are preferentially expressed in beta cells and are expressed on the surface in sufficient amounts to enable imaging. They have extracellular domains against which a naturally occurring ligand, a peptide or and antibody (or antibody fragment) can be developed as tracer. The selected biomarkers will not be modified in conditions of inflammation. These unique features will make clinical analysis of beta cell mass possible.

The goal of the biomarkers of the present invention is their use in the estimation and visualisation of the pancreatic beta cell mass in health and diseased state (diabetes or following islet transplantation). The invention will allow the development of tools for prediction and follow up of the diabetic state, for the follow up of islet transplantation, and as surrogate markers for therapeutic assays aiming to prevent diabetes and/or regenerate beta cell mass. The non-invasive imaging performed with these candidates will allow the detection of the increase of decrease in beta cell mass.

The invention therefore provides a non-invasive method for the diagnosis or prognosis of a diabetic disorder such as type 1 or type 2 diabetes mellitus (T1D or T2D) or hyperinsulinemia, by detecting and/or measuring the beta cell mass of a subject and comparing it to a reference amount of beta cell mass of a healthy subject. An increase of the beta cell mass in the subject under investigation points to a condition of hyperinsulinemia, while a reduction of the beta cell mass in the subject under investigation points to a condition of diabetes mellitus of type 1 or 2.

The non-invasive method for the diagnosis or prognosis of a diabetic disorder encompasses the highly specific detection and/or visualization of beta cells through the detection of beta cell-specific biomarker selected from the group of FXYD2-gamma-a, FXYD2-gamma-b and FXYD2-gamma-c.

The detection of the specific markers is done by using a radioisotopically labelled tracer molecule that binds the biomarker with high specificity. Tracers may for example be antibodies, or their fragments, single chain antibodies, nanobodies, affybodies, aptamers, photoaptamers, a specific ligand or interacting protein, or any small molecule or the like that has been shown to specifically bind the biomarker of choice.

The antibodies can be known or commercially available antibodies or can be specifically designed to detect one of the biomarkers of the invention in a highly specific manner.

In this respect, the inventors designed polyclonal antibody preparations directed to:
the gamma-a splice variant of FXYD2 by immunizing rabbits with the 11AA peptide of SEQ ID NO 1 (MT-GLSMDGGGS+C-KLH), designated as antibodies SPY393 and SPY394,
or the 15 AA peptide of SEQ ID NO:2 (MT-GLSMDGGGSPKGD+C-KLH),
or the 28 AA peptide of SEQ ID NO:3 (MT-GLSMDGGGSPKGDVDPFYYDYETVRN+C-KLH),
the gamma b splice variant of FXYD2 by immunizing rabbits with the peptide of SEQ ID NO 4 (MDRW-YLGGS+C-KLH), designated antibody SPY341,
the gamma c splice variant of FXYD2 by immunizing rabbits with the peptide of SEQ ID NO 5

(GKPGPLRTLPEPSGPLPPSSGLSQPQVHALCPLSPLVTTGCCGQAAE

RDSCWERPPIPLLLPSLSG + C-KLH),

It is important to note that the sequence recognized by the SPY393 and 394 antibodies in the human FXYD2-gamma-a is 100% similar to the sequence of the monkey (*Macaca mulata*) FXYD2-gamma-a. This enables us to test the characteristics of the labeled antibody in *Macaca mulata*, and to extrapolate the results obtained in said monkey model to the human situation.

In one embodiment, the diagnostic or prognostic method of the invention uses Positron Emission Tomography (PET), a nuclear medicine medical imaging technique which produces a three-dimensional image or map of functional processes in the body. The system detects pairs of gamma rays emitted indirectly by a positron-emitting radioisotope, which is introduced into the body through a tracer molecule e.g. a specific biomarker binding molecule. Images of the radioisotope labeled tracer in the body are then reconstructed by computer analysis. In modern scanners, a PET scan is combined with a CT X-ray scan (PET-CT) performed on the patient at the same time, in the same machine, providing the structural reference of the organs etc.

In an alternative embodiment, single photon emission computed tomography (SPECT) imaging can be used in the diagnostic or prognostic method of the invention. SPECT uses a gamma camera to acquire multiple 2-D projections from multiple angles. A computer is then used to apply a tomographic reconstruction algorithm to the multiple projections, yielding a 3-D dataset. This dataset may then be manipulated to show thin slices along any chosen axis of the body.

Preferred labels used in PET or PET-CT are short-lived radioisoptopes such as carbon-11 (~20 min), nitrogen-13 (~10 min), oxygen-15 (~2 min), and fluorine-18 (~110 min) or medium-lived radioisotopes such as iodine-124 (~4 days) when appropriate.

A typical in vivo diagnostic method encompassed by the invention is as follows:
a) introducing an isotopically labelled tracer molecule, specifically binding to said marker into a subject
b) the in vivo visualisation of a tracer molecule specifically binding to the beta cells in the pancreas using PET, PET-CT or SPECT,
c) quantification of the beta cells mass in said subject
d) comparison of the beta cell mass data obtained in step c) with the beta cell mass of a healthy subject,
d) diagnosing the subject as having diabetes or being at risk of having diabetes when the level of beta cell mass obtained in step c) is reduced as compared to that of a healthy subject and diagnosing the subject as having hyperinsulinemia or being at risk of having hyperinsulinemia when the level of beta cell mass obtained in step c) is increased as compared to that of a healthy subject.

The method of in vivo diagnosis or prognosis can be used to diagnose insulin-related disorders such as type 1 or type 2 diabetes mellitus, hyperinsulinemia and pancreatic cancer such as the occurrence of neuroendocrine tumors of the pancreas like insulinoma derived from the beta cells.

For treating insulin-related disorders, pancreatic islet transplantation is an option. Typically, the Edmonton protocol is applied wherein specialized enzymes are used to remove islets from the pancreas of a deceased donor. Because the islets are fragile, transplantation occurs soon after they are removed. Typically a patient receives at least 10,000 islet "equivalents" per kilogram of body weight, extracted from two donor pancreases. Patients often require two transplants to achieve insulin independence. Some transplants have used fewer islet equivalents taken from a single donated pancreas. Transplants are often performed by a radiologist, who uses x rays and ultrasound to guide placement of a catheter through the upper abdomen and into the portal vein of the liver. The islets are then infused slowly through the catheter into the liver. The patient receives a local anesthetic and a sedative. In some cases, a surgeon may perform the transplant through a small incision, using general anesthesia.

The key of success for such a beta cell transplantation treatment is of course the purity of the beta cell preparation used for the transplantation. The invention provides for methods of specifically isolating beta cells for use in islet transplantation and tools for follow up of transplanted beta cells.

In a further embodiment, the invention provides for methods to isolate and/or purify pancreatic beta cells from pancreatic tissue, by visualizing or labeling the beta cells in a specific manner using one or more biomarkers selected from the group of FXYD2-gamma-a, FXYD2-gamma-b and FXYD2-gamma-c.

Alternatively, the method provides a method for identification of stem cell populations in order to derive functional insulin-expressing cells comprising the following steps:
a) tagging the treated stem cells with a labeled binding molecule specifically directed to the marker FXYD2-gamma,
b) isolating the labeled cells from the non-labeled cells through the tag on the potential beta stem cells, thereby obtaining a substantially pure beta stem cell preparation. The method of the invention can in certain embodiments further comprise the steps of:
c) performing immunohistochemistry to identify the number of beta stem cells, and to define the new beta cell mass and
d) follow up of therapeutic strategies and detect newly formed beta cell mass.

The above separation methods can for example be performed by separating labelled cells from non-labelled cells using standard separation techniques based on the retention of labelled binding molecules directed to one or more of the biomarkers of the present invention.

One option is to use antibodies, aptamers, oligonucleotides or other specific binding agents or ligands, directed to one of the biomarkers of the invention, for tagging cells of interest with a small magnetic particle or magnetic bead. The bead-binding molecule conjugate is then directed to the beta-cells in the pancreatic cell preparation and the beta cells can be specifically purified from the total pancreatic cell preparation by using e.g. an electromagnetic field. In some systems, the sample is processed through a column that generates a magnetic field when placed within the separator instrument, retaining only the labeled cells.

Other systems offer simplified versions of the magnetic separator. Instead of a column and separator instrument, these systems use a simple magnet to directly retain the labeled cells within the tube, while the supernatant is drawn off. Some of these systems can be used in a positive or negative selection manner. Negative or enrichment selection means that unwanted cells can be labeled (captured), leaving the cells of interest label-free. The magnetic particles do not interfere with flow cytometry, nor do they interfere with cell growth, according to Hammonds, so cells that have been isolated using such a system can be further cultured.

Magnetic separation has proven uniquely powerful and broadly applicable, sometimes leading to 70% recovery of the target cells and up to 98% purity while retaining cell viability.

Alternatively, an efficient non-magnetic separation method, based on work on tetrameric antibody complexes (TACs) works by linking unwanted cells in a sample together, forming clumps. After labeling, the sample is layered over a buoyant density medium such as Ficoll. The labeled cells pellet with when centrifuged, while the desired, unlabeled cells are recovered at the interface. This method is fast and the cells obtained are not labeled with antibodies and are untouched.

Many of these techniques are most powerful in combination. The skilled person would however be aware of other methods to selectively purify specific cell-types.

The term "binding molecules" used in the methods and kits of the invention refers to all suitable binding molecules that are specifically binding or interacting with one of the biomarkers of the invention and that can be used in the methods and kits of the present invention. Examples of suitable binding agents are antibodies, monoclonal- or polyclonal antibodies, nanobodies, affybodies, antibody fragments, aptamers, photoaptamers, oligonucleotides, lipocalins, specifically interacting small molecules, Molecular Imprinting Polymers (MIPs), DARPins, ankyrins, specifically interacting proteins, peptidomimetics, biomimetics or peptides, and other molecules that specifically bind to one of the biomarkers. Both monoclonal, polyclonal or single chain antibodies or fragments thereof that bind one of the biomarkers of the present invention are useful in the methods and kits of the present invention. The monoclonal and polyclonal antibodies can be prepared by methods known in the art and are often commercially available.

Aptamers that bind specifically to the biomarkers of the invention can be obtained using the so called SELEX or Systematic Evolution of Ligands by EXponential enrichment. In this system, multiple rounds of selection and amplification can be used to select for DNA or RNA molecules with high specificity for a target of choice, developed by Larry Gold and coworkers and described in U.S. Pat. No. 6,329,145. Recently a more refined method of designing co-called photoaptamers with even higher specificity has been described in U.S. Pat. No. 6,458,539 by the group of Larry Gold.

Methods of identifying binding agents such as interacting proteins and small molecules are also known in the art. Examples are two-hybrid analysis, immunoprecipitation methods and the like.

In addition, the invention also provides tools and methods for the identification of binding molecules, such as peptides or small molecules, monoclonal- or polyclonal antibodies, nanobodies, affybodies, antibody fragments, aptamers, photoaptamers, lipocalins, specifically interacting small molecules, Molecular Imprinting Polymers (MIPs), DARPins, ankyrins, specifically interacting proteins or peptides, and other molecules that specifically bind to one of the biomarkers, using cells or cell-lines that do or do not express the FXYD2-gamma marker. To this end, the invention provides several FXYD2-gamma-positive cells and/or cell-lines (rodent pancreatic islets, rat INS-1E, AR42J cells and in human CAPAN-2 cells) and one FXYD2-gamma negative cell-line (human PANC-1 cells). These cells or cell-lines can be used to screen for binding agents or compounds that specifically bind to FXYD2-gamma-positive cells, but not to FXYD2-gamma negative cells in order to identify new tracer molecules for visualization of beta-cell mass in PET, PET-CT or SPECT analysis.

In one such aspect, the invention provides a method for identifying new tracer molecules that specifically bind FXYD2-positive cells comprising the steps of:

a) contacting the candidate tracer molecule with the FXYD2-gamma positive cell-type or cell-line and measure the interaction between the candidate tracer molecule and the cells;

b) contacting the candidate tracer molecule with the FXYD2-gamma negative cell-type or cell-line and measure the interaction between the candidate tracer molecule and the cells;

c) wherein these candidate tracer molecules that bind the cells of step a) but not the cells of step b) are retained as beta-cell-mass tracer molecules. In a preferred embodiment of said method, the FXYD2-gamma positive cell-type or cell-line is selected from the group consisting of: rodent pancreatic islets, rat INS-1E, AR42J cells and in human CAPAN-2 cells; and the FXYD2-gamma negative cell-type or cell-line is PANC-1.

The invention further provides kits for identifying new tracer molecules that specifically bind FXYD2-positive cells comprising two cell types or cell-lines, one being an FXYD2-gamma positive cell-type or cell-line and one being an FXYD2-gamma-negative cell-type or cell-line. In a preferred embodiment, the FXYD2-gamma positive cell-type or cell-line is selected from the group consisting of: rodent pancreatic islets, rat INS-1E, AR42J cells and in human CAPAN-2 cells; and the FXYD2-gamma negative cell-type or cell-line is PANC-1.

In addition to the use of cell-lines, biochemical binding assays known in the art using the FXYD2-gamma biomarker as a target can also be used.

The term "label" includes all suitable isotopic labels for use in PET, PET-CT or SPECT analysis, labels suitable for specific extraction such as magnetic or paramagnetic beads, labels suitable for diagnosis in vitro such as fluorescent dyes or other luminescent labels, known in the art.

The term "beta cell related disorder" described in the methods or uses or kits of the invention encompasses all disorders related to beta cells such as: type 1 diabetes mellitus, type 2 diabetes mellitus, hyperinsulinemia, obesity, neuroendocrine tumors or occurrence of insulinoma.

Additionally, the biomarkers of the invention can also be used in in-vitro methods for the analysis of the amount or characteristics of beta cells in a cell culture, either obtained from a biopsy or from a cell-line derived culture. Beta-cell specific markers of the invention can further be used to characterize the differentiation state of cells such as modified stem cells, differentiated in vitro as beta cells.

In all embodiments of the invention, the term "FXYD2-gamma" includes the isoforms FXYD2-gamma-a, FXYD2-gamma-b and FXYD2-gamma-c.

EXAMPLES

The invention is illustrated by the following non-limiting examples

Example 1

Selection Strategy for the Identification of Beta Cell Specific Plasma Membrane Proteins The strategy used in these examples is depicted in FIGS. 1 and 2. The pancreas is composed of 1-2% of tiny endocrine islets of Langerhans which are scattered in the exocrine tissue. The exocrine pancreas consists of acinar cells and a network of ducts. Islets contain insulin secreting beta cells and non beta cells, e.g. the glucagon secreting alpha cells, pancreatic polypeptide producing PP cells and somatostatin secreting delta cells. Pancreatic beta cells are selectively destroyed by an autoimmune assault in T1D, and there is also evidence that beta cell loss is present in long term T2D, albeit at a lower level than in T1D. Gene expression data on pancreatic islets and on pancreatic beta cells have been obtained in the last 8 years. The methods used are microarray analysis and massive parallel signature sequencing (a procedure that detects gene expression based on sequencing of signatures derived from expressed sequences). The data obtained with MPSS are quantitative (transcripts per million) and more sensitive than array analysis (transcripts as low as three copies per cell can be detected). To obtain the beta cell gene expression profile we performed MPSS in two independent human islet samples, while microarray data was obtained on FACS-purified rat primary beta cells and non beta cells. Human islets used for MPSS were of excellent quality: the beta cell percentages of the two preparations were 53 and 59%. The MPSS data obtained showed 5662 genes in sample 1, and 5929 genes in sample 2 at a level of at least 5 tpm. A gene was considered as 80% or more specific to pancreatic islets if its signature count in islets were equal to or greater than 80% of the total count of signatures across the other 32 tissues examined (including pancreas) at a minimum level of 20 tpm. Insulin is at the top of the list with an average level of 126753 tpm; this is 13% of the entire mRNA population in the human islet samples. Islet-specific transcripts, following the criteria described above, were obtained by comparing the expression levels observed in pancreatic islets to a published MPSS dataset from 32 human tissues (LICR MPSS dataset: http://mpss.licr.org/). We detected a total of 940 genes that are relatively specific to pancreatic islets, and 324 of these genes are expressed at higher levels in rat pancreatic β cells as compared to α cells. Using the TMHMM program, proteins with transmembrane regions were identified and 44 proteins were retained. These candidates were further analysed for plasma membrane location (via literature, GO and IPA analysis) and the expression levels were analyzed in conditions of inflammation, i.e. after exposure to cytokines or viruses (own microarray data). The expression level of these genes was also examined in T-cells/lymphocytes based on the GNF symatlas website (http://symatlas.gnf.org/SymAtlas/). For the microarray analysis we used FACS sorted islet cells: the purity of primary β cells in the beta cell fraction was 90% while the non-beta cell fraction contained mostly α cells (75-85%). The results indicate that there are 6,190-6,270 genes expressed in rat β, α, and INS-1 cells (threshold average signal intensity=250, target intensity=1500). Differential expression analysis of genes expressed in β vs non-β cells resulted in 983 genes that are enriched in β-cells (fold enrichment≧2, FDR 5%). There were 972 genes that were more highly expressed in β-cells as compared to non β-cells (fold enrichment≧2).

The islet specific MPSS list and the beta cell specific gene list obtained by microarray were introduced in the Ingenuity Pathway Analysis software and we then selected plasma membranes and proteins allocated as "unknown". By this procedure we obtained 121 plasma membrane proteins and 249 unknown proteins. We compared expression levels in islets versus total pancreas and selected genes that had more than 10 tpm (expression level of Glucokinase in islets) and had expression levels that were more than 50 fold amplified in islets versus total pancreas. We checked their expression levels in 32 other tissues. This comparison resulted in 55 islet-specific membrane proteins. Using the microarray data we selected the proteins that had higher expression levels in beta cells than in non-beta cells and identified 12 non-beta cell specific genes (data not shown). Comparing our microarray data obtained with primary beta cells in control versus 24 h exposure to cytokines (500 u/ml IFNγ+100 u/ml IL1β), we omitted genes that were induced or severely inhibited after exposure to cytokines. Using the Symatlas open resource (http://symatlas.gnf.org/SymAtlas) we removed genes that were highly expressed in T-cells and other cells of the immune system which will be present in the islets during the process of insulitis. Literature analysis of all candidates was performed, and candidates previously identified as auto-antigens were omitted, since endogenous auto-antibodies may interfere with the tracers used for beta cell imaging. A final group of 12 beta cell specific membrane proteins and 2 new islet-specific membrane proteins were selected and are shown below in Table 1. The strategy described above is depicted schematically in FIG. 1.

TABLE 1

List of selected candidates in collaboration with ISB (Seattle, USA).

| Entrez gene ID | name | MPSS | | microarray data | | | |
|---|---|---|---|---|---|---|---|
| | | islets | pancreas | beta cells | non beta | FC b/non b | inflammation |
| 486 | FXYD2 | 1750 | 3 | 52 | 38 | 1.4 | D |
| 2778 | GNAS/Xlas | 21772 | 17 | 156433 | 123478 | 1.3 | NC |
| 2778 | GNAS/Alex | 21772 | 17 | 156433 | 123478 | 1.3 | NC |
| 10423 | CDIPT | 556 | 0 | 8881 | 3962 | 2.2 | NC |
| 10493 | VAT1 | 507 | 0 | 4898 | 2446 | 2.0 | D |

TABLE 1-continued

List of selected candidates in collaboration with ISB (Seattle, USA).

| Entrez gene ID | name | MPSS islets | MPSS pancreas | microarray data beta cells | microarray data non beta | microarray data FC b/non b | microarray data inflammation |
|---|---|---|---|---|---|---|---|
| 22883 | CLSTN1 | 307 | 0 | 7071 | 2878 | 2.5 | NC |
| 8140 | SLC7A5 | 240 | 0 | 4437 | 1752 | 2.5 | NC |
| 2017 | CTTN | 200 | 0 | 10024 | 3475 | 2.9 | D |
| 8938 | BAIAP3 | 194 | 0 | | | | |
| 116372 | LYPD1 | 187 | 0 | 77 | 7 | 10.8 | NC |
| 310 | ANXA7 | 175 | 0 | 3760 | 2853 | 1.3 | NC |
| 1755 | DMBT1 | 148 | 0 | 78 | 31 | 2.5 | D |
| 57662 | KIAA1543 | 104 | 0 | | | | |
| 23428 | SLC7A8 | 88 | 0 | 2744 | 1379 | 2.0 | NC |

D: decreased;
NC: not changed;
FC; Fold change

Example 2

Validation of the Islet Specific Expression of the Selected Biomarkers

A. Marker FXYD2:

MPSS data obtained in human islets compared to expression in 32 human tissues derived from the LICR MPSS dataset; only expression levels above 5 tpm are shown.

A.1 Introduction:

The gamma-subunit of the Na, K-ATPase (FXYD2, ATP1G1, HOMG2, MGC12372) is a single-span membrane protein that regulates the Na, K-ATPase by modifying its kinetic properties. The gamma-subunit belongs to a family of 7 FXYD proteins which are tissue specifically expressed (FIG. 1 after Cornelius F et al, 2003). FXYD2 is abundantly expressed in the proximal and distal tubules and in the medullary thick ascending limb of Henle of the kidney (Arystarkhova E et al 2002, Pihakaski-Maunsbach K et al 2006). Two splice variants (gamma-a (SEQ ID NO: 6) and gamma-b SEQ ID NO:7) have been detected in rat and human (Arystarkhova E et al 2005) while the third splice variant gamma-c has been characterized only in mouse (Holstead Jones D et al, 2005). Recently a further splice variant of FXYD2 has been deposited in the GenBank database (NM_001127489, 2747 bp, 145 AA=14.5 kDa (SEQ ID NO:8), designated as the human FXYD2-gamma-c splice variant. This new splice variant appears to an alternatively spliced form of the FXYD2-gamma-a protein, since it has an identical amino terminus of 21 amino acid residues (FIG. 2B). Interstingly, this new gamma-c variant (SEQ ID NO:8) is also recognised by the antibody made by the inventors SPY393.

The inventors subsequently investigated whether this new gamma-c variant is expressed in human CAPAN2 cells and in human islet cells. Additionally, the inventors used immunoprecipitation on CAPAN2 cells using a SPY393 F(ab)2-biotine binding agent and strept-Dynabeads In order to sequence the protein of 20 kD which was consistently detected with the SPY393 antibody.

The inventors subsequently produced an antibody which specifically binds the new gamma-c variant.

Three human FXYD2 splice variants have been characterized; form gamma-a and gamma-b differ only in the N-terminal 8 aa. For the gamma-b peptide the sequence is conserved between rat, human and mouse. The sequence is not conserved for the gamma-a (see FIG. 2). This new splice variant appears to an alternatively spliced form of the FXYD2-gamma-a protein, since it has an identical amino terminus of 21 amino acid residues, a large insert in the middle of the protein and a different C-terminus. The sequence is depicted in SEQ ID NO:8.

A.2 Expression of FXYD2 is Islet-Specific

Figure 3:
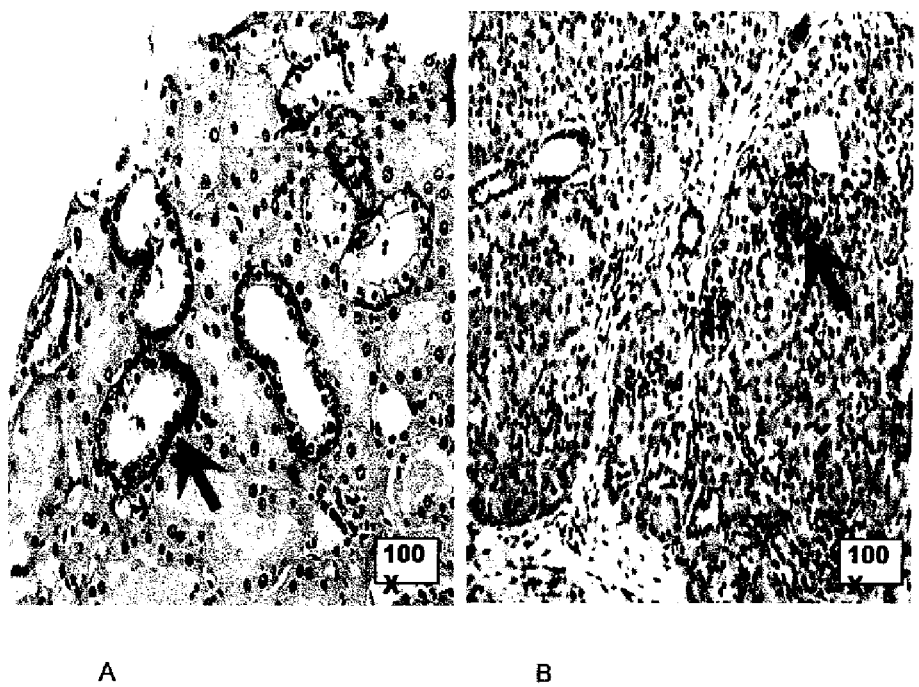
FIG. 3: Immunohistochemistry performed on slices of human kidney clear cell carcinoma and on slices of normal human pancreas with the Abnova monoclonal antibody directed against FXYD2 gamma. The black arrow marks staining in kidney while the white arrow shows staining specifically to the islets of Langerhans in the pancreas.

FXYD2 Gamma-b:

Validation of this candidate was initiated with the only available commercial monoclonal antibody raised against the full length gamma-b splice variant from Abnova (clone 1C3-B3). Immunohistochemistry on pancreas and kidney slices confirmed the presence of FXYD2 gamma-b in the kidney (FIG. 3a). The expression of FXYD2 in the pancreas was restricted to the pancreatic islets and to rare intercaled ducts in the exocrine tissue (FIG. 3b). Expression of FXYD2 in the pancreas and, more specifically, in the pancreatic islet has never been shown.

Figure 4:
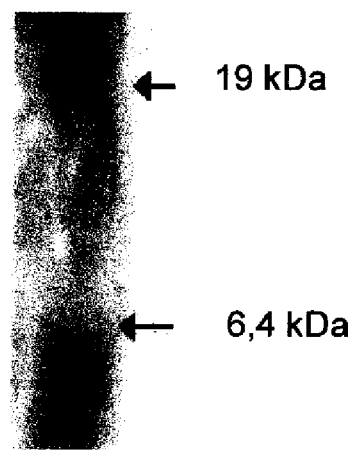
FIG. 4: FXYD2 gamma expressed in rat pancreatic dispersed islet cells. Abnova monoclonal antibody directed against FXYD2 gamma was used to detect FXYD2 gamma in 100.000 rat dispersed islet cells via Western Blotting. The given molecular weight is approximative.

In rat dispersed islets analysed by Western Blotting, the Abnova antibody detected weakly 2 bands (approximatively 19 kDa and approximatively 6.4 kDa see FIG. 4) for FXYD2.

FXYD2 Gamma-a:

Since no antibody was available to analyze the human gamma-a splice variant alone, rabbit polyclonal antibodies were raised (collaboration with Eurogentec) against the N-terminal fragments of gamma-a and gamma-b human FXYD2 splice variants.

```
MTGLSMDGGGS + C                  (SEQ ID NO: 1) =
gamma-a peptide 1

MTGLSMDGGGSPKGD                  (SEQ ID NO: 2) =
gamma-a peptide 2

MTGLSMDGGGSPKGDVDPFYYDYETVRN     (SEQ ID NO: 3) =
gamma-a peptide 3,

MDRWYLGGS + C                    (SEQ ID NO: 4) =
gamma-b peptide

Xxx                              (SEQ ID NO: 5) =
gamma-c peptide
```

For this purpose, two rabbits were injected per peptide. The rabbit SPY393 and SPY394 polyclonal antibodies recognize the gamma-a FXYD2 peptide (SPY394 also detects to a lesser extent the gamma-b FXYD2 peptide). The SPY341 antibody recognizes the gamma-b FXYD2 peptide. These antibodies were validated in rat, mouse and human tissues.

The gamma-b peptide selected for antibody production is similar for human, rat and mouse and the antibodies SPY341 and SPY342 should be able to detect FXYD2 in these different species. Our human gamma-a peptide (11 AA) differs 4

AA with the rat gamma-a peptide (11 AA); The mouse gamma-a peptide is longer (15 AA) and differs 9 AA with our selected human gamma-a peptide (see FIG. 2A). The C-terminal part of both selected peptides, used to produce antibodies, is similar and can result in an antibody detecting both peptides.

Figure 5:
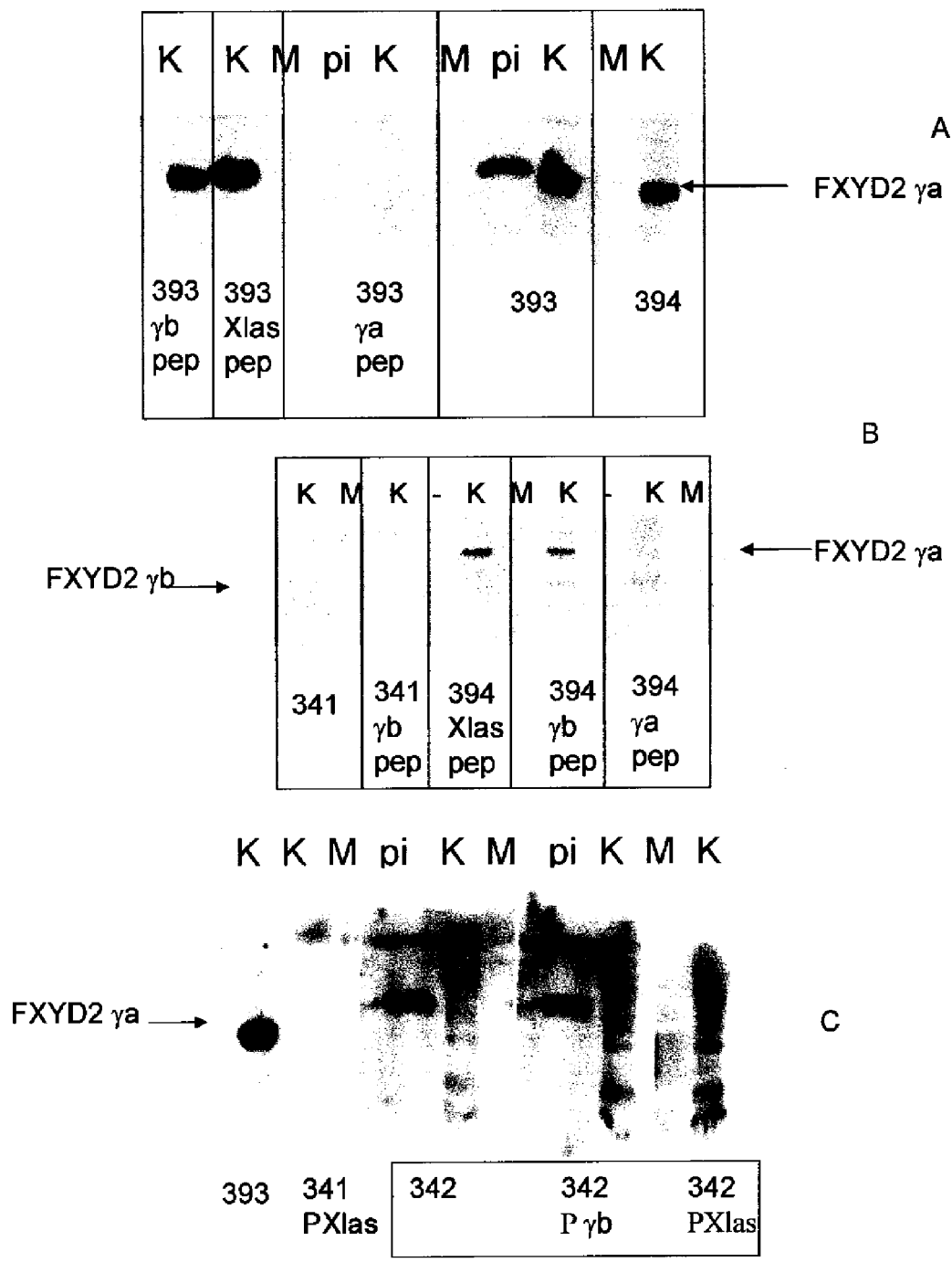
FIG. 5: FXYD2 gamma expression in rat kidney (K) and rat pancreatic islets (pi); M is the molecular weight marker. Polyclonal antibodies against the N-terminal peptides of FXYD2 gamma-a (SPY393 and SPY394) or gamma-b (SPY 341 and SPY342) were analyzed via Western blotting. The antibodies were either applied directly or were first preincubated for 1 h with a 10 fold overload of its specific peptide gamma-a or gamma-b or a peptide of non specific origin (Xlas pep), centrifuged and used for Western blotting.

To detect if the antibody 393 could be used in biodistribution studies for preliminary results in rodents (rat or mouse) we tested the antibody in Western blotting. Western blotting with the SPY393 and SPY394 antibodies on rat total kidney protein (taken as positive control) and on rat dispersed pancreatic islet cells showed a specific band of approximatively 19 kDa. This signal is specifically blocked by preincubation with an 10 fold overload of gamma-a peptide (FIG. 5A). With the SPY341 and SPY394 antibodies we detected a very week signal, of around 6.4 kDa, which can be blocked with a 10 fold overload of gamma-b peptide (FIG. 5B). The SPY342 did not detect specific binding that could be blocked with either gamma-a or gamma-b peptide (FIG. 5C).

Figure 6:
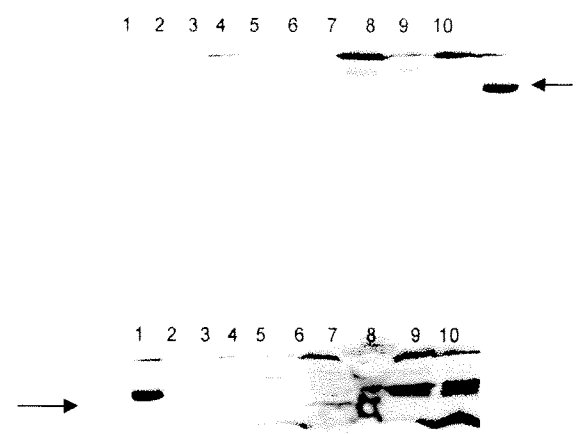
FIG. 6: Detection of FXYD2 in different mouse tissues. FXYD2 is specifically detected in mouse pancreatic islets. Upper panel: 1: marker; 2: rat kidney (positive control); 3: mouse brain; 4: mouse liver; 5: mouse spleen; 6: mouse stomach; 7: mouse intestine; 8: mouse colon; 9: mouse islets; 10: marker. Lower panel: 1: rat kidney; 2: marker; 3: mouse lung; 4: mouse muscle; 5: mouse heart; 6: mouse exocrine; 7: AR42J cell line; 8: INS-1$^E$ cell line.

As the sequence used to produce the antibody against the FXYD2 gamma-a differs in human versus mouse, we isolated different mouse tissues and analyzed SPY393 binding by Western Blotting. From all tissues analyzed, only mouse pancreatic islets showed a specific FXYD2 band. (see FIG. 6)

To determine whether the rabbit polyclonal antibodies detect specifically FXYD2 in the pancreatic islets, without major binding to exocrine cells (which could result in high background levels), the antibodies were tested by immunohistochemistry on normal human pancreas. SPY393 antibody stains specifically the pancreatic islets without background in the exocrine pancreas. SPY394 detects the FXYD2 gamma-a but the staining is less intense than the staining observed with the SPY393 antibody, confirming the results seen in Western Blotting (FIG. 7). SPY341 detects FXYD2 gamma-b specifically in pancreatic islets but the staining is less intense than observed with SPY393. The antibody SPY342 did not stain the pancreas (results not shown).

Expression Levels of the Biomarkers in Other Tissues as Compared to Human Islets Based on the MPSS data, FXYD2 expression is specifically detected in islets, kidney and salivary gland with low expression detected in other tissues (see Table 2 below). There was no detection in Adrenal Gland, Bone Marrow, Brain, Pituitary, Placenta, Prostate, Small Intestine, Spinal cord, Thyroid, Trachea, Colon and Monocytes. The MPSS data (cf. Table 3) show a more than 500 fold amplification of the signal in pancreatic islets versus total pancreas. As pancreatic islets represent 1-2% of the total pancreatic mass this candidate is selected as islet-specific.

To confirm the MPSS data, immunohistochemistry was performed on 35 different human tissues (Tissue Micro array or TMA); results are shown in Table 2). These TMA were tested with the commercial anti-FXYD2 antibody and with our SPY393 anti-FXYD2 antibody. Staining with our SPY393 antibody was only shown in the pancreatic islets of pancreas and not in any of the other human tissue sections.

FXYD2-Gamma-c Expression Data

SEQ ID No:3 Peptide Used for Immunization

Table 2: Comparison of commercial anti-FXYD2 antibody (Abnova) and SPY-393 anti-FXYD2 antibody of the invention.

| | Anti-FXDY2 (Abnova antibody) Normal Tissue | | | Anti-FXDY2 (SPY-393 antibody) Normal Tissue | | |
|---|---|---|---|---|---|---|
| Organ | Number of case | FXYD2-Staining | Number of positive cases | Number of case | FXYD2-Staining | Number of pos. cases |
| Stomach | 6 | neg | | Stomach | neg | |
| Duodenum | 1 | neg | | Duodenum | neg | |
| Ileon | 3 | neg | | Ileon | neg | |
| Jejenum | 2 | neg | | Jejenum | neg | |
| Appendix | 2 | neg | | Appendix | neg | |
| Colon | 9 | neg | | Colon | neg | |
| Pancreas | 4 | pos | 4 | Pancreas | pos | 4 |
| VB | 1 | neg | | VB | neg | |
| Endometrium | 3 | neg | | Endometrium | neg | |
| Myometrium | 2 | neg | | Myometrium | neg | |
| Ovarium | 6 | neg | | Ovarium | neg | |
| Fallopian tube | 4 | neg | | Fallopian tube | neg | |
| IVG | 7 | neg | | IVG | neg | |
| Placenta | 1 | neg | | Placenta | neg | |
| Blood | 1 | neg | | Blood | neg | |
| Skin | 4 | neg | | Skin | neg | |
| GGL | 3 | neg | | GGL | neg | |
| Prostate | 7 | neg | | Prostate | neg | |
| Kidney | 6 | pos | 4 weak | Kidney | neg | |
| VS | 4 | neg | | VS | neg | |
| Thymus | 2 | neg | | Thymus | neg | |
| Vagina | 1 | neg | | Vagina | neg | |
| Thyroid | 5 | neg | | Thyroid | neg | |
| Testicles | 4 | neg | | Testicles | neg | |
| Epilon | 1 | neg | | Epilon | neg | |
| Spleen | 2 | pos | | Spleen | pos | |
| Bladder | 4 | neg | | Bladder | neg | |
| Amygdales | 2 | neg | | Amygdales | neg | |
| Blood | 6 | neg | | Blood | neg | |
| Adrenal Gland | 1 | neg | | Adrenal Gland | neg | |
| Liver | 3 | neg | | Liver | neg | |

-continued

| | Anti-FXDY2 (Abnova antibody) Normal Tissue | | | Anti-FXDY2 (SPY-393 antibody) Normal Tissue | | |
|---|---|---|---|---|---|---|
| Organ | Number of case | FXYD2-Staining | Number of positive cases | Number of case | FXYD2-Staining | Number of pos. cases |
| Brain | 2 | neg | | Brain | | neg |
| Lung | 3 | neg | | Lung | | neg |
| Uterus | 3 | neg | | Uterus | | neg |
| Oesophagus | 3 | neg | | Oesophagus | | neg |

TABLE 3

MPSS data:
Human MPSS data: in
transcripts per million (tpm)

| | |
|---|---|
| islets | 1750 tpm |
| pancreas | 3 tpm |
| Kidney | 47 tpm |
| Salivary Gland | 45 tpm |
| Bladder | 9 tpm |
| Mammary gland | 8 tpm |
| Thymus | 7 tpm |
| Lung | 5 tpm |
| A | |

All other tissues <5 tpm

A.3. Expression of FXYD2 is Restricted to the Beta Cells in the Pancreatic Islets Expression levels of FXYD2 in other tissues were derived from Microarray Symatlas data for the FXYD2 205674_x_at probeset showing expression in pancreatic islets, kidney and MOLT4 cells (see weblink: http://symatlas.gnf.org/SymAtlas/) cf. Table 6 for corresponding MPSS date. To validate that FXYD2 expression is detected specifically in beta cells, immunohistochemistry was performed in consecutive pancreas slices that were analyzed with the SPY393 antibody directed against FXYD2, anti-insulin antibody (detecting beta cells) or anti-glucagon antibody (detecting alpha cells); pancreas paraffin sections of 3 μm (see FIG. 8).

Figure 9A:
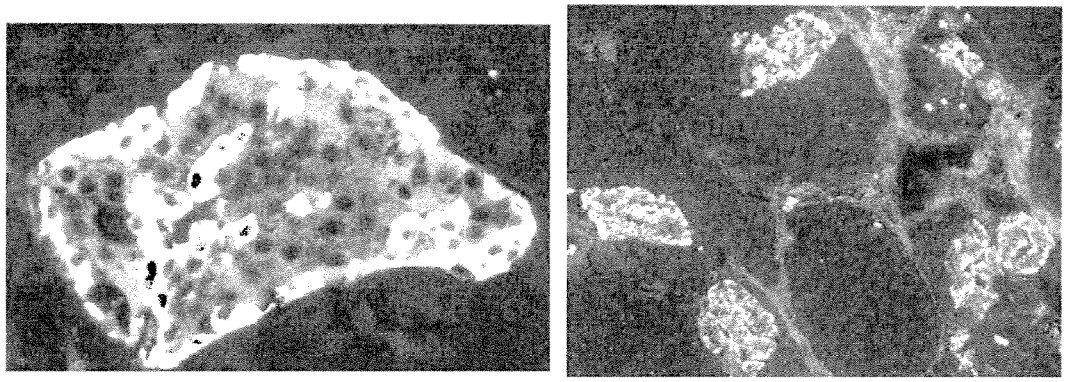
Figure 9B:
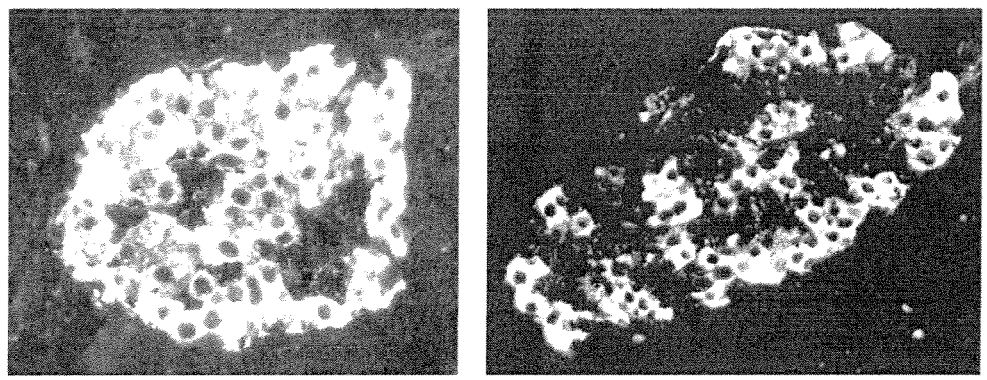

To validate that FXYD2 was specifically expressed in beta cells, we performed immunofluorescence (see FIG. 9 and Tables 4 and 5 for percentage colocalisation). For this purpose, the SPY393 antibody with an anti-rabbit IgG-TRITC label (red) was used either in combination with a monoclonal antibody against glucagon (K79bB10, Sigma cf. FIG. 9a) or in combination with a monoclonal antibody against insulin (K36aC10, DBS cf. FIG. 9b). The mouse monoclonal antibodies were detected with a anti-mouse IgG-FITC labelled (green). No colocalisation was seen between the glucagon expressing a cells and FXYD2 (cf. Table 4), while the insulin-expressing β-cells all co-localized with FXYD2 (cf. Table 5). This shows a preferential expression of FXYD2 gamma-a in the pancreatic beta cells.

TABLE 4

Percentage of colocalisation of glucagon with FXYD2γa (FIG. 12a)

| | | Glucagon | FXYD2γa | Colocalisation | TOTAL |
|---|---|---|---|---|---|
| PHOTO 1 | Counter 1 | 56 | 90 | 1 | 147 |
| | Counter 2 | 52 | 74 | 0 | 126 |
| PHOTO 2 | Counter 1 | 22 | 103 | 1 | 126 |
| | Counter 2 | 23 | 92 | 0 | 115 |

TABLE 4-continued

Percentage of colocalisation of glucagon with FXYD2γa (FIG. 12a)

| | | Glucagon | FXYD2γa | Colocalisation | TOTAL |
|---|---|---|---|---|---|
| PHOTO 3 | Counter 1 | 16 | 46 | 7 | 69 |
| | Counter 2 | 14 | 66 | 3 | 83 |
| TOTAL | | 183 | 471 | 12 | 666 |
| % | | 27.5 | 70.7 | 1.8 | 100 |

TABLE 5

Percentage of colocalisation for insulin and FXYD2γa (FIG. 12b)

| | | Insulin | FXYD2γa | Colocalisation | TOTAL |
|---|---|---|---|---|---|
| PHOTO 1 | Counter 1 | 9 | 1 | 107 | 117 |
| | Counter 2 | 12 | 0 | 95 | 107 |
| PHOTO 2 | Counter 1 | 14 | 3 | 60 | 77 |
| | Counter 2 | 20 | 1 | 44 | 65 |
| PHOTO 3 | Counter 1 | 8 | 1 | 92 | 101 |
| | Counter 2 | 8 | 0 | 83 | 91 |
| TOTAL | | 71 | 6 | 481 | 558 |
| % | | 12.7 | 1.1 | 86.2 | 100 |

A.4. Expression Levels of FXYD2 are not Induced in Inflammation Conditions.

The Beta Cell Gene Expression Bank is an open resource created by the inventors containing microarray experiments performed in the Laboratory of Experimental Medicine. Microarray expression values were obtained in human islets, rat primary beta cells and INS-1E cells comparing control versus inflammation conditions (either induced by cytokines or by virus exposure). Microarray data were obtained on isolated human islets exposed for 48 h to either IL-1β (50 U/ml) and IFN-γ (1000 U/ml) or coxsackievirus 5B; multiplicity of infection 30-100 (Ylipaasto P et al, 2005). Analysis of the human datasets showed a twofold decrease in FXYD2 expression when exposed to cytokines and this decrease was lower when exposed to CBV5 (see Table 6). These data were confirming the MPSS data showing a 2 to 3 fold reduction of FXYD2 expression after exposure to cytokines for 48 h. Probesets in the rat microarray were scoring low, this is probably due to bad selection of probesets.

TABLE 6

Influence of inflammation or virus infection on the expression levels of FXYD2 in human pancreatic islets.
FXYD2: in human pancreatic islets (fold change compared to control)

| Probe | Mean Expression level (+/−SF) | Treatment | Probe | 48 h |
|---|---|---|---|---|
| 205674_x_at | 192.9 +/− 33.3 | IL-1β + IFNγ | 205674_x_at | 0.5 ± 0.1[a] |
| 207434_s_at | 122.6 +/− 20.1 |  | 207434_s_at | 0.8 ± 0.1[a] |
|  |  | coxsackievirus B5 | 205674_x_at | 0.8 ± 0.0[a] |
|  |  |  | 207434_s_at | 0.7 ± 0.0[a] |

For comparison, expression of insulin and glucokinase are respectively 1785 ± 22 and 45 ± 5 in isolated human islet cells (n = 3).
Isolated human islets were exposed for 48 h to either IL-1β (50 U/ml) and IFN-γ (1000 U/ml) or CBV-5 (coxsackievirus 5B; multiplicity of infection 30-100).
Results are fold change compared to controls.
[a]Mean ± SEM of 3 chip determinations from 3 individual donor samples.

Protein levels of FXYD2 were analysed in INS-1E and AR42J cells in control condition and in cytokine (IL1β+IFNγ) induced conditions via Western Blotting, no changes in FXYD2γ a were detected (FIGS. 16C and D).

A.5. FXYD2 is Detected on the Membrane and Cytosol of the Pancreatic Beta Cells.

Analysis by histochemistry shows both membrane and cytoplasmic expression of FXYD2 (see previous figures and FIG. 10). Immunocytochemistry performed on rat and mouse dispersed pancreatic islets without perturbing the plasma membrane (without the use of paraformaldehyde and Triton X100) showed detection of FXYD2 on the membrane of the cells.

In FIG. 12, we show that the expression of FXYD2 gamma-a is drastically decreased in islets from type 1 diabetes patients (CO and TELF; these codes identify two patients, deceased respectively 3 days and 5 years after the diagnosis of type 1 diabetes) compared to normal pancreas (CTRL). Consecutive sections of 3 μm were taken and stained with SPY393 antibody, anti-insulin antibody or anti-glucagon antibody. In the TELF pancreas, beta cells can not be detected based on insulin staining; this was correlated with disappearance of FXYD2 staining. In the CO pancreas, beta cells can not be detected based on insulin staining but a very faint staining of FXYD2 remained (magnification 1000×).

In FIG. 13, the amounts of the FXYD2 gamma-a in islets from type 1 diabetes patients: 20 Langerhans islets/case were quantified; % of stained tissue area (Labelling Index—LI) and mean staining intensity. As seen in the FIG. 14 above: in the TELF pancreas: FXYD2 staining completely disappeared and this correlated with the disappearance of beta cells as identified by insulin staining. In the CO pancreas staining for insulin disappeared and this correlated with a 50 fold decreased staining for FXYD2 gamma-a when comparing the labeling index (LI) with CTRL.

B. Markers Alex and XLas

B.1. Introduction

Alternative gene product encoded by XL-exon (Alex) and Guanine nucleotide-binding G(s) subunit alpha isoforms extra large (XLas) are two proteins encoded by the GNAS1 locus (Abramowitz J et al, 2004) through use of an alternative first exon and promoter. Gs-alpha and Xlas have different N-terminal domains but are identical over the carboxy-terminal portion. Unlike the widely expressed Gs-alpha, XLas has a limited tissue distribution. It is mainly found in neuroendocrine tissues with very high levels in pituitary (Kehlenbach R H et al, 1994, Pasolli H et al, 2000). Xlas is a Gs protein involved in signalling of several Gs-coupled receptors such as class B parathyroid hormone receptor 1, CRF receptor 1, b2-adrenergic receptor, TSH receptor (Bastepe M et al, 2002).

Xlas has also been located in the plasma membrane (Pasolli H et al, 2000). Alex is a proline-rich plasma membrane protein of 356 amino acids that is predominantly associated with cell membrane ruffles. It interacts with the extra large N-terminal region of Xlas. Like XLas it is expressed in neuroendocrine cells (Klemke M et al, 2001).

B2. Alex and XLas are Expressed in Pancreatic Islets.

MPSS data show a 1200 fold enriched expression of the GNAS1 locus in pancreatic islets when compared to total pancreas. Therefore these 2 proteins were selected for protein validation.

As no commercial antibody was available for the human proteins and rat and human sequences differ considerably, we selected the specific peptides to produce rabbit polyclonal antibodies (Eurogentec).

```
XLas:   PAEEMETEPPHNEPI    (SEQ ID NO: 9)

Alex:   RREEKYPLRGTDPLP    (SEQ ID NO: 10)
```

Two rabbits were injected per peptide. Rabbit polyclonal antibodies SPY343 and SPY344 are targeted against Xlas and antibodies SPY345 and SPY346 are targeted against Alex. As human and rat sequences differ to much we could not validate the antibodies in Western Blotting. The antibodies were validated on human pancreas by immunohistochemistry. Rabbit polyclonal antibody SPY343 and SPY344 both detected Xlas specifically in the pancreatic islets in human paraffin pancreas sections, with SPY344 giving the best results (see FIG. 18, different magnifications).

Further validation to confirm preferential expression in human pancreatic islets versus pancreas surrounding tissues by performing human tissue microarrays is proceeding.

Similarly the specific location of XLas and Alex to the pancreatic beta cells is being analysed by performing colocalisation with anti-insulin or with anti-glucagon antibodies.

B3. Expression Levels are not Increased in Conditions of Inflammation.

The Beta Cell Gene Expression Bank is an open resource created by the inventors containing microarray experiments performed in the Laboratory of Experimental Medicine. Analysis of the microarray data performed on isolated human islets exposed for 48 h to either IL-1β (50 U/ml) and IFN-γ (1000 U/ml) or coxsackievirus 5B; multiplicity of infection 30-100 (Ylipaasto P. et al, 2005) showed no induction of the GNAS locus in conditions of inflammation. These results can be seen on the following weblink:

http://dil.t1dbase.org/page/GeneMore/display/?ug_id=Rn.127731.

Further validation of XLas and Alex in conditions of inflammation will be performed in pancreas sections of human T1D.

C. Marker VAT1: Vesicle Amine Transport Protein 1 Homolog (Hs.514199)

VAT1 is a membrane protein detected in synaptic vesicles, responsible for regulating the storage and release of neurotransmitters in the nerve terminal. VMAT1 and VMAT2 expression was reported in the endocrine pancreas and in pancreatic tumors (Anlauf et al, 2003). Rabbit polyclonal antibodies against VMAT1 showed expression in the endocrine duct cells. This information is however conflicting with the information obtained in our MPSS data where we see no expression in total pancreas and an expression of 507 tpm in pancreatic islets. In purified rat primary beta cells expression level are high and 2 fold increased in beta cells. Exposure to inflammation conditions decreases VAT1 expression.

C1. Own Results: MPSS Data on Human Islets and Microarray Data Obtained in Rat Primary Beta Vs Non-Beta Cells:

| | MPSS | | microarray data | | |
|---|---|---|---|---|---|
| name | islets | pancreas | beta cells | non beta | FC b/non b |
| VAT1 | 507 | 0 | 4898 | 2446 | 2.0 |

C2. Expression of VAT1 is not Induced During Conditions of Inflammation:

See results on the following web link:
http://dil.t1dbase.org/page/GeneMore/display/?ug_id=Rn.9118

C3. Beta Cell Gene Bank Information:

The gene is highly expressed in spinal cord, lung and pancreatic beta cells: see weblink: http://dil.t1dbase.org/page/GeneOverview/display/?gene_id=10493

C4. GNF Symatlas Information: http://symatlas.gnf.org/SymAtlas/ (FIG. 16)

D. Marker CDIPT: CDP-Diacylglycerol-Inositol 3-Phosphatidyltransferase (Hs.121549)

CDIPT (MGC1328, PIS, PIS1, Pis, Pis1) catalyzes a formation of phosphatidylinositol from CDP-diacylglycerol (Saito S et al, 1998). It is expressed in brain and retina. In pancreatic islets it is enriched in secretory granule membranes (Rana R S et al, 1986). In our MPSS data its expression is enriched in pancreatic islets versus total pancreas. Expression levels in rat pancreatic beta cells are high and are 2 fold enriched versus non beta cells. In inflammation conditions, CDIPT expression is reduced both in MPSS data on human islets and microarray data in human islets.

D1. Own Results: MPSS Data on Human Islets and Microarray Data Obtained in Rat Primary Beta Vs Non-Beta Cells:

| | MPSS | | microarray data | | |
|---|---|---|---|---|---|
| name | islets | pancreas | beta cells | non beta | FC b/non b |
| CDIPT | 556 | 0 | 8881 | 3962 | 2.2 |

D2. Expression of CDIPT is not Induced in Conditions of Inflammation:

See results in the Beta Cell Gene Bank
(http://dil.t1dbase.org/page/GeneMore/display/?ug_id=Rn.10598)
http://dil.t1dbase.org/page/GeneOverview/display/?gene_id=10423

D3. GNF Symatlas Information: http://symatlas.gnf.org/SymAtlas/ (FIG. 17)

E. Marker BAIAP3: BAI1-Associated Protein 3 (Hs.458-427)

BAIAP3 (BAP3) is a protein implicated in regulated exocytosis (Palmer R E et al. 2002), it has been reported to be induced by a novel transcription factor, EWS-WT1 in Desmoplastic small round cell tumor (DSRCT). It has not been reported as expressed in pancreatic islets. No probeset is available on rat microarrays. In human islets its expression is enhanced in islets versus total pancreas, in the microarray data obtained in human islets expression levels are in the range of glucokinase. Exposure to cytokines reduces BAIAP3 expression in human islets (MPSS data)

| | | MPSS | | microarray data | | |
|---|---|---|---|---|---|---|
| unigene | name | islets | pancreas | beta cells | non beta | FC b/non b |
| 8938 | BAIAP3 | 194 | 0 | no data available | | |

E1. Own Microarray Information: BAIAP3 is not Influenced by Inflammation and Expressed in Beta Cells and not in Pancreas Surrounding Tissues.

See weblink: http://dil.t1dbase.org/page/GeneMore/display/?ug_id=Rn.201777
http://dil.t1dbase.org/page/GeneOverview/display/?gene_id=8938

E2. GNF Symatlas Information: the Probeset in the GNF Symatlas Showed High Expression in Brain and Pituitary. http://symatlas.gnf.org/SymAtlas/ (FIG. 18)

F. Marker CLSTN1: Calsyntenin 1 (Hs.29665)

CLSTN1 is a postsynaptic single-pass type I membrane protein with a cytoplasmic calcium-binding domain (Vogt L. et al, 2001). Calsyntenin-1 docks vesicular cargo to kinesin-1 (Koneca A et al, 2006). By electron microscopy, the calsyntenin protein family was localized in the postsynaptic membrane of excitatory central nervous system (CNS) synapses. In situ hybridization analysis showed that CLSTN1 was abundant in most neurons of the central nervous system (Hintsch G. et al, 2002). In our MPSS data, CLSTN1 expression is enriched in pancreatic islets versus pancreas, it is highly expressed in rat primary beta cells and enriched 2.5 fold in beta versus non beta cells. Exposure of human islets to inflammatory conditions decreases CLSTN1 expression in human islets (MPSS data).

| | | MPSS | | microarray data | | |
|---|---|---|---|---|---|---|
| unigene | name | islets | pancreas | beta cells | non beta | FC b/non b |
| 22883 | CLSTN1 | 307 | 0 | 7071 | 2878 | 2.5 |

F1. Own Microarray Information:

CLSTN1 expression is not influenced by inflammation see weblink http://dil.t1dbase.org/page/GeneMore/display/?ug_id=Rn.99876 http://dil.t1dbase.org/page/GeneOverview/display/?gene_id=22883

F2. GNF Symatlas Information: http://symatlas.gnf.org/SymAtlas/ (FIG. 19)

G. Marker SLC7A5: Solute Carrier Family 7

SLC7A5 (cationic amino acid transporter, y+ system, member 5 or LAT1) is a plasma membrane transporter important for the import of large neutral amino acids with branched or aromatic side chains. In our MPSS data, its expression is enriched in human islets versus total pancreas. It is highly expressed in rat pancreatic beta cells and more than 2 fold increased in beta cells compared to non beta cells. Its expression is not induced in rat primary beta cells exposed to cytokines. Exposure of human islets to cytokines decreases LAT1 expression (MPSS data).

| | | MPSS | | microarray data | | |
|---|---|---|---|---|---|---|
| unigene | name | islets | pancreas | beta cells | non beta | FC b/non b |
| 8140 | SLC7A5 | 240 | 0 | 4437 | 1752 | 2.5 |

G1. SLC7A5 Expression is not Influenced by Inflammation

See weblink: http://dil.t1dbase.org/page/GeneMore/display/?ug_id=Rn.32261 http://dil.t1dbase.org/page/GeneOverview/display/?gene_id=8140

G2. Symatlas Information (http://symatlas.gnf.org/SymAtlas/): Expression is Higher in Islets than in Total Pancreas and is Found in Restricted Population of Cells. (FIG. 20)

H. Marker CTTN: Cortactin (Hs.632133)

Cortactin CTTN, EMS1) is a regulator of dynamic actin networks. It is located in the membrane and involved in vesicle transport and in cell-cell adhesion and cell spreading. Recently it was shown that in head and neck tumours squamous cell carcinoma cells cortactin overexpression promotes resistance to the EGFR kinase inhibitor gefitinib (Timpson P et al, 2007). It has not been reported as expressed in pancreatic islets. In our MPSS data, CTTN is enriched in pancreatic islets versus total pancreas. Expression levels in primary beta cells are high and almost 3 fold enriched in beta cells versus non beta cells. Exposure of human islets to inflammation conditions decreases CTTN expression both in MPSS data and microarray data.

| | | MPSS | | microarray data | | |
|---|---|---|---|---|---|---|
| unigene | name | islets | pancreas | beta cells | non beta | FC b/non b |
| | CTTN | 200 | 0 | 10024 | 3475 | 2.9 |

H1. Expression of CTTN is not Induced by Inflammation

See weblink http://dil.t1dbase.org/page/GeneMore/display/?ug_id=Rn.107869 http://dil.t1dbase.org/page/GeneOverview/display/?gene_id=2017

H2. GNF symatlas information (http://symatlas.gnf.org/SymAtlas/): the information found in Synatlas does not confirm our data that CTTN is enriched in pancreatic islets, the probeset score low which can be due to selection of a bad probeset.

I. Marker LYPD1: LY6/PLAUR: Domain Containing 1 (Hs.651252)

The LYPD1 (or PHTS putative Hela tumor suppressor) antisense gene is highly expressed throughout the central nervous system (Egerod K L et al, 2007). It was reported to overlap with the 3' exon of the GPR39 gene. It contains an N-terminal signal sequence and a leukocyte antigen-6 (Ly6)/u PAR (PLAUR; domain characteristic of glycosylphosphatidylinositol-linked cell surface glycoproteins. Overexpression of LYPD1 reduced cell survival in Hela cells (Yu D. et al, 2006). In our MPSS data, LYPD1 is enriched in pancreatic islets versus total pancreas. Expression levels in rat primary beta cells are not high but are more than 10 fold enriched in beta versus non beta cells.

| | | MPSS | | microarray data | | |
|---|---|---|---|---|---|---|
| unigene | name | islets | pancreas | beta cells | non beta | FC b/non b |
| 116372 | LYPD1 | 187 | 0 | 77 | 7 | 10.8 |

I1. Beta Cell Gene Bank Information:

http://dil.t1dbase.org/page/GeneOverview/display/?gene_id=72585

J. Marker ANXA7: Annexin A7 (Hs.631827);

Annexin A7 (Anx7) or synexin is a calcium-dependent membrane-binding protein that fuses membranes but can act as a voltage-dependent calcium channel (Caohuy H et al, 1996). Anx7 is required for nutritional control of gene expression in mouse pancreatic islets of Langerhans (Srivastava M et al, 1999 and 2002). The null phenotype was lethal at embryonic day 10. Heterozygous mice were viable and fertile, but showed a defect in insulin secretion and an increased insulin content within isolated pancreatic islets. These mice have a profound reduction in inositol-1,4,5-triphosphate (IP3) receptor function in pancreatic islets. Different splice variants have been characterized with tissue specific expression (Magendzo, K et al, 1991). Annexin 7 mobilizes calcium from endoplasmic reticulum stores in brain (Watson W D. Et al, 2004). Anx7 is enriched in pancreatic islets versus total pancreas. In rat primary beta cells it is highly expressed and enriched in beta versus alpha cells. Exposure to cytokines does not increase ANXA7 expression in human islets (MPSS data).

J1. Our Expression Analysis:

| | | MPSS | | microarray data | | |
|---|---|---|---|---|---|---|
| unigene | name | islets | pancreas | beta cells | non beta | FC b/non b |
| 310 | ANXA7 | 175 | 0 | 3760 | 2853 | 1.3 |

J2. Our Beta Cell Gene Bank Information:
http://dil.t1dbase.org/page/GeneOverview/display/?gene_id=310

J3. GNF Synatlas Probes Gave Low Expression Levels in Human and were not Taken into Account.

K. Marker DMBT1: Deleted in Malignant Brain Tumors 1 (Hs.279611)

DMBT1 (GP340, muclin, Crpd) also called surfactant pulmonary-associated protein D-binding protein is a novel member of the scavenger-receptor superfamily (Holmskov et al 1997). Mutations of the DMBT1 gene have been reported in human astrocytic gliomas (Mollenhauer, J. et al, 1997 and Mueller W. et al, 2002). Different isoforms have tissue-specific expression; expression has been reported in alveolar and macrophage tissues. A loss or reduction of DMBT1 expression was seen in esophageal, gastric, lung and colorectal carcinomas. In our MPSS data, DMBT1 is enriched in pancreatic islets versus total pancreas. Expression levels in rat primary beta cells are not high but are more than 2 fold enriched in beta versus non beta cells.

Exposure of human islets to cytokines reduces DMBT1 expression (MPSS data).

K1. Our Expression Analysis MPSS Data:

|  |  | MPSS | | microarray data | | |
|  |  | | | beta | non | |
| unigene | name | islets | pancreas | cells | beta | FC b/non b |
| --- | --- | --- | --- | --- | --- | --- |
| 1755 | DMBT1 | 148 | 0 | 78 | 31 | 2.5 |

K2. Own Microarray Information: DMBT1 Expression See Weblink
http://dil.t1dbase.org/page/GeneMore/display/?ug_id=Rn.10107
http://dil.t1dbase.org/page/GeneMore/display/?ug_id=Rn.10107
http://dil.t1dbase.org/page/GeneOverview/display/?gene_id=1755

L. Marker KIAA1543: RIKEN cDNA 2310057J16 Gene (Hs.17686)

KIAA1543 was cloned from a cDNA library of human brain (Nagase T. et al, 2000), it has not been identified in pancreas. Its function is unknown. In our MPSS data, its expression is enriched in pancreatic islets versus total pancreas. No probeset is available on human and rat microarrays. Exposure of human islets to cytokines has no effect on its expression (MPSS data).

|  |  | MPSS | | microarray data | | |
|  |  | | | beta | non | |
| unigene | name | islets | pancreas | cells | beta | FC b/non b |
| --- | --- | --- | --- | --- | --- | --- |
| 57662 | KIAA1543 | 104 | 0 | no data available | | |

L1. Beta Cell Gene Bank Information:
http://dil.t1dbase.org/page/GeneOverview/display/?gene_id=57662

M. Marker SLC7A8: Solute Carrier Family 7 (Cationic Amino Acid Transporter, y+ System), Member 8 (Hs.632348)

SLC7A8 or LAT2 (or Linker for activation of T-cells family member 2 (Non-T-cell activation linker) (Williams-Beuren syndrome chromosome region 15 protein). is a 535-amino acid protein with 12 transmembrane domains, with the N and C termini intracytoplasmic. Coexpression of SLC7A8 with the 4F2 heavy chain brings SLC7A8 to the plasma membrane and induces an amino acid transport activity with broad specificity for small and large zwitterionic amino acids (Pineda, M et al, 1999). Highest expression was reported in kidney, the dopamine precursor L-dihydroxyphenylalanine is transported through LAT2 (Quinones H. et al, 2004). Overexpression of renal LAT1 and LAT2 enhanced L-DOPA uptake in immortalized renal proximal tubular cells (Pinho L W et al, 2003 and 2004). Expression of LAT2 is enriched in pancreatic islets versus total pancreas (MPSS data). Expression levels in rat primary beta cells are high and 2-fold increased in beta versus non beta cells.

M1. Own MPSS Human Data Expression Analysis:

|  |  | MPSS | | microarray data | | |
|  |  | | | beta | non | |
| unigene | name | islets | pancreas | cells | beta | FC b/non b |
| --- | --- | --- | --- | --- | --- | --- |
| 23428 | SLC7A8 | 88 | 0 | 2744 | 1379 | 2.0 |

M2. Beta Cell Gene Expression Information: Expression is Highest in Kidney and Pancreatic Islets.
http://dil.t1dbase.org/page/GeneOverview/display/?gene_id=23428

M3. Symatlas Information: http://symatlas.gnf.org/SymAtlas/ (FIG. 21)

In conclusion, a group of 12 beta cell specific and 2 new islet specific plasma membrane proteins have been identified. The top 3 (FXYD2, Alex and Xlas) were selected to set up the validation strategy. All three candidates were specifically enriched in the pancreatic islets and located specifically to the islets in the pancreas. FXYD2 is only expressed in the pancreatic beta cells and is detected in the plasma membrane. All 3 candidates are not induced in conditions of inflammation.

Example 3

Confirmation of a Marked Decrease in FXYD Expression in the Pancreas of Two Type 1 Diabetic Patients Expression of FXYD2 gamma-a is drastically decreased in islets from type 1 diabetes patients (CO and TELF; these codes identify two patients, deceased respectively 3 days and 5 years after the diagnosis of type 1 diabetes) compared to normal pancreas (CTRL). Consecutive sections of 3 μm were taken and stained with SPY393 antibody, anti-insulin antibody or anti-glucagon antibody. In the TELF pancreas, beta cells can not be detected based on insulin staining; this was correlated with disappearance of FXYD2 staining. In the CO pancreas, beta cells can not be detected based on insulin staining but a very faint staining of FXYD2 remained (cf. FIG. 12, magnification 1000×).

FIG. 13 shows the quantification of the FXYD2 gamma-a in islets from type 1 diabetes patients: 20 Langerhans islets/case were quantified; % of stained tissue area (Labelling Index—LI) and mean staining intensity. As seen in the FIG. 11 above: in the TELF pancreas: FXYD2 staining completely disappeared and this correlated with the disappearance of beta cells as identified by insulin staining. In the CO pancreas staining for insulin disappeared and this correlated with a 50 fold decreased staining for FXYD2 gamma-a when comparing the labeling index (LI) with CTRL.

FIG. 14 indicates that decreased FXYD2-gamma-a expression correlates with beta-cell loss in STZ-treated *Macaca mulatta*. Consecutive sections of pancreas from control (A-C, CT) and STZ-treated *Macaca mulatta* (D-F, primate 1 and G-I, primate 2) were analysed with anti-glucagon antibody (left column A, D, G), anti-insulin antibody (middle column B, E, H) or SPY393 polyclonal anti-FXYD2-gamma-a (right column C, F, I). Magnification 400×.

In addition, a significant decrease in insulin and FXYD2-gamma-a expression in the pancreas of STZ-induced diabetic *Macaca mulatta* could be demonstrated (FIG. 15). Pancreas sections from control (CT) and STZ-induced diabetic *Macaca mulatta* (Primate P1-6) were analysed. Six islets per case were counted by three observers unaware of sample identity. Glucagon positive, insulin positive and FXYD2-gamma-a positive cells were calculated as relative percentage per islet; Values in CT were considered as 100%. Percentage of cells stained for insulin, glucagon and FXYD2-gamma-a in STZ-treated *Macaca mulatta* and non-treated control (CT) are represented in Table 7 below. Pancreas sections from control primate (CT) and STZ-induced diabetic *Macaca mulatta* pancreas (Primate 1-6) were analyzed. The number of beta-cells were counted as percentage cells of total pancreas. Six islets per case were counted by three observers unaware of sample identity. Glucagon positive, insulin positive and SPY393 positive cells were calculated as relative percentage of positive cells per islet.

TABLE 7

Percentage of cells stained for insulin, glucagon and FXYD2-gamma-a in STZ-treated *Macaca mulatta* and non-treated control (CT).

| N° | β-cells as % of total pancreas | Averaged per monkey % ± SD | | |
|---|---|---|---|---|
| | | insulin | glucagon | FXYD2γa |
| CT | 2.57 | 54.9 ± 13.1 | 55.1 ± 8.1 | 59.5 ± 8.7 |
| Primate 1 | 0.39 | 12.4 ± 6.4 | 68.3 ± 7.5 | 14.3 ± 7.0 |

TABLE 7-continued

Percentage of cells stained for insulin, glucagon and FXYD2-gamma-a in STZ-treated *Macaca mulatta* and non-treated control (CT).

| N° | β-cells as % of total pancreas | Averaged per monkey % ± SD | | |
|---|---|---|---|---|
| | | insulin | glucagon | FXYD2γa |
| Primate 2 | 0.24 | 23.4 ± 11.1 | 68.1 ± 3.3 | 10.6 ± 4.0 |
| Primate 3 | 0.20 | 7.2 ± 6.5 | 80.1 ± 10.1 | 2.3 ± 2.0 |
| Primate 4 | 0.20 | 22.0 ± 13.7 | 68.3 ± 7.1 | 11.3 ± 9.5 |
| Primate 5 | 0.17 | 12.4 ± 6.4 | 69.6 ± 4.3 | 4.5 ± 0.6 |
| Primate 6 | 0.06 | 12.6 ± 4.9 | 72.0 ± 10.4 | 4.0 ± 3.0 |

Example 4

Biodistribution Studies in Rodents to Confirm that the Selected Candidates can be Used for Imaging Pancreatic Beta Cell Mass The SPY393 antibody can be labeled with any radioactive tracer to perform biodistribution studies. In this particular example, $^{124}$I was used. A monoclonal antibody can also be developed for FXYD2 and after validation, this antibody and its fragments can also be used in a biodistribution study. Methods for making monoclonal antibodies are well known in the art.

Figure 17A:
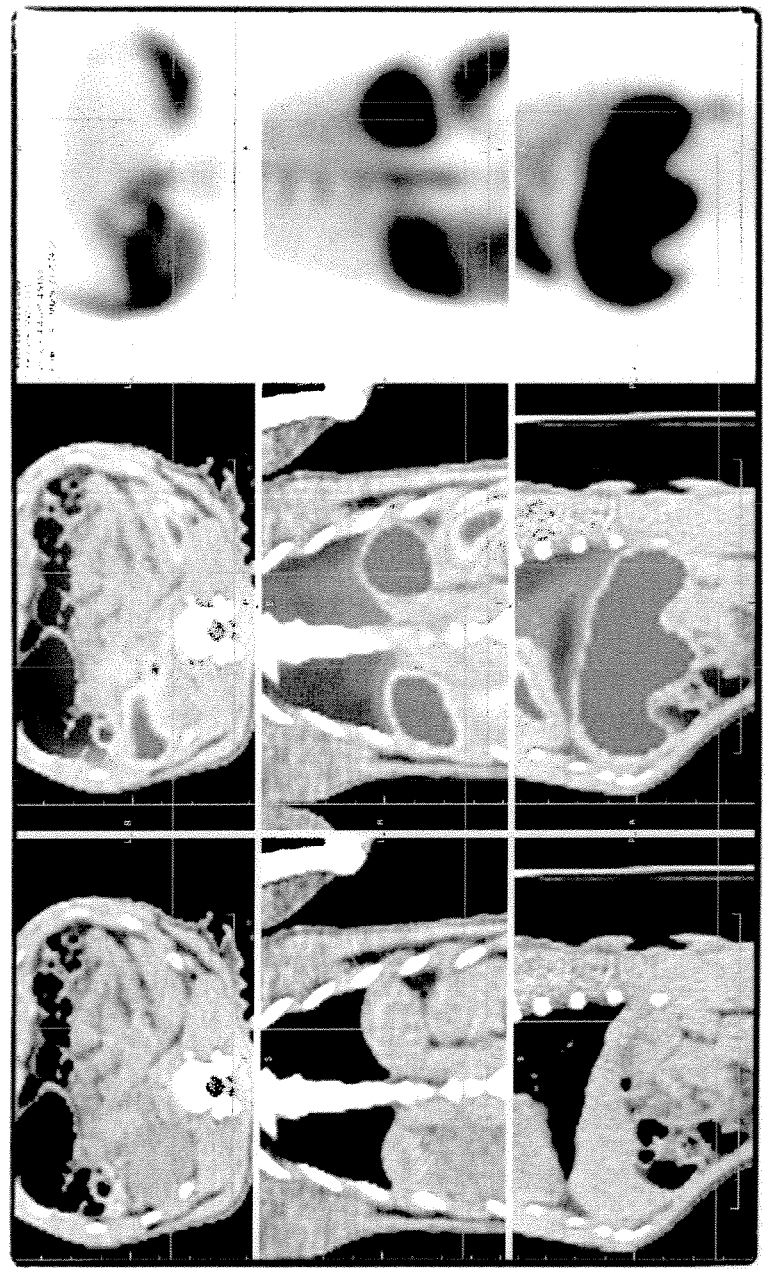
Figure 17B:
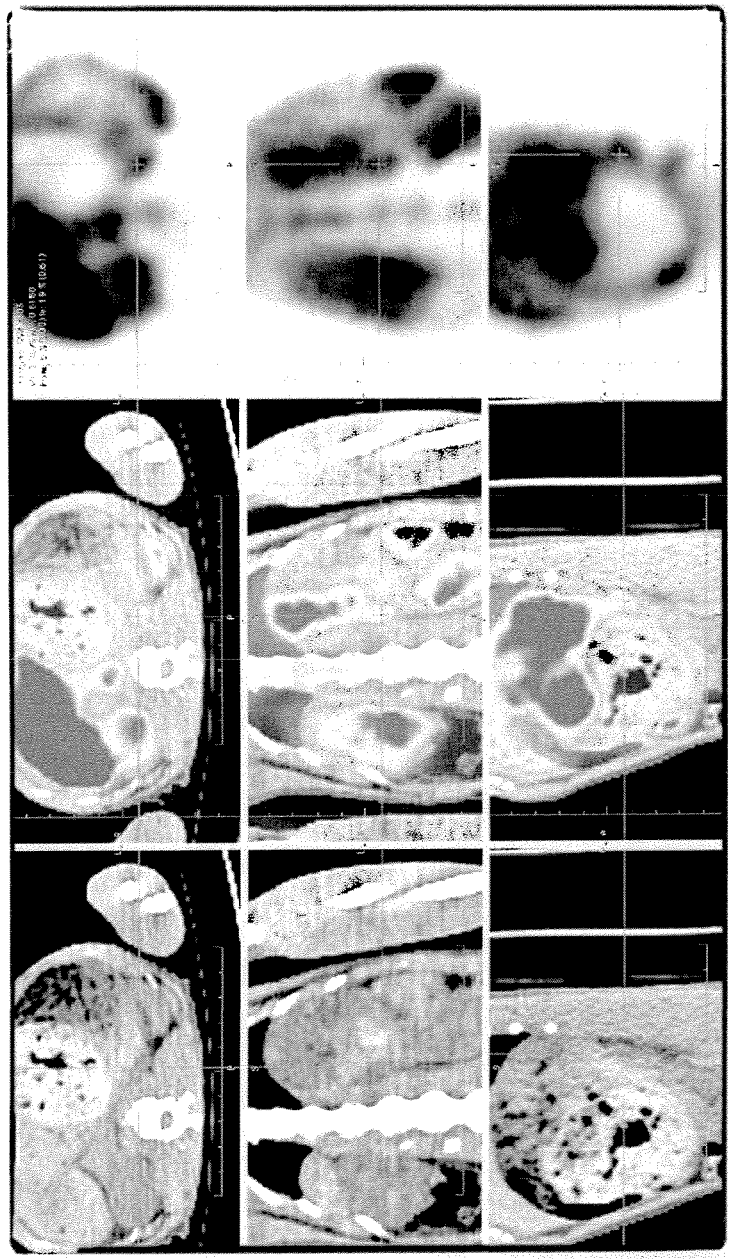
Figure 17C:
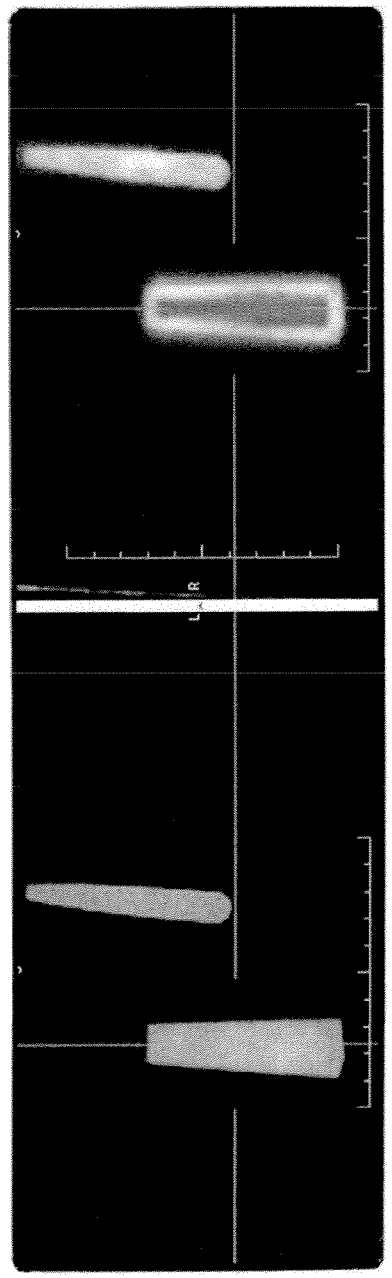

The results of a first biodistribution study in *Macaca mulatta* are shown in FIG. 17. The animals were injected with SPY393 antibody labeled with $^{124}$I. PET scans were performed at different time points after the injection. The results are also given in Table 8 below. As can be seen from the figures, the pancreas is indeed targeted (Day 1, FIG. 17A and day 2, FIG. 17B), but the signal is somewhat hidden due to staining of the stomach content (cf. FIG. 17C). New scans are performed to reduce this background.

These first experiments in any case show without doubt that the FXYD2-gamma marker is a very promising target for beta-cell mass determination and visualization in the body of a mammal.

TABLE 8

Experiment performed at UCL collaboration with Max Lonneux/F. Jamar and Denis Dufrane. SPY393 labeled with I124

| | Time (postinjection) | PET/CT: | Result: |
|---|---|---|---|
| Day 1 (4/11) | Time 0 (17 h) | 1 h scan abdomen | Kidney/Liver/Aorta/Heart |
| | Time 3 h (20 h) FIG. 17A | 40 min (whole body) | Lung not positive Kidney/Liver/Thyroid/Aorta/Heart Upper part of stomach |
| Day 2 (5/11) | Time 24 h (17 h) FIG. 17B | 40 min (whole body) | Lung very faintly positieve Liver, Kidney, Stomach, Thyroid Tail of the pancreas Blood was taken to measure free I124 |
| Day 3 (6/11) | Time 48 h (17 h) | 40 min (whole body) | Lung not positive Liver, Kidney, Thyroid and very big stomach Due to stomach pancreas signal can not be seen |
| Day 4 (7/11) | Time 72 h (17 h) | 40 min (whole body) | Medication was given to empty stomach content of stomach was radioactive (PET) (FIG. 17C) Liver, kidney, stomach fainter and diffuse signal in pancreas |

TABLE 8-continued

Experiment performed at UCL collaboration with Max Lonneux/F. Jamar and Denis Dufrane. SPY393 labeled with I124

| Time (postinjection) | | PET/CT: | Result: |
|---|---|---|---|
| Day 7 (10/11) | Time 144 h (17 h) (day 6) | 40 min (whole body) | Less experience person took scan Stomach not cleared overshadows picture |
| Day 9 (12/11) | | 9 h: Monkey was anesthesized. Liver, Kidney, Spleen, Stomach Pancreas Head, Body and Tail was isolated and pictures from position organs were taken Samples of these radioactive tissues in OCT and in liquid N2 were made for autoradiography analysis. | |

Example 5

Identification of Small Molecules Specifically Binding with FXYD2-Gamma-Positive Cells In another aspect, the invention provides a method fro the identification of small molecules that specifically bind with FXYD2-gamma-positive cells. Such small molecules (e.g. peptides, chemical compounds and the like) can then be use as tracers for visualizing beta-cell mass. To this end, the inventors identified human cell-lines which either did or did not express the FXYD2 biomarker.

As indicated in FIG. 16, expression of FXYD2-gamma-a and -gamma-b isoforms could be shown in rodent pancreatic islets, rat INS-1E, AR42J cells and in human CAPAN-2 cells but not in human PANC-1 cells. FXYD2-gamma-a expression is not changed after 24 h exposure to cytokines, which confirms that the method used to select the beta-cell markers indeed is cytokine-expression independent.

- A FXYD2-gamma-a and -gamma-b splice variants were detected in mouse pancreatic islets. Primers were used to detect FXYD2-gamma-a isoform (lane 1), FXYD2-gamma-b isoform (lane 2) and FXYD2-gamma-c isoform (lane 3); Marker (M; lane 4). Importantly, the gamma-c variant was not detected.
- B The polyclonal anti-FXYD2-gamma-a antibody (SPY393) recognizes only the FXYD2-gamma-a isoform. Rat dispersed pancreatic islet cells (lanes 3, 5) and rat kidney (lanes 1, 2, 4, 6) were analysed. Lane 1 SPY393 with FXYD2-gamma-b blocking peptide, lane 2 SPY393 with an aspecific blocking peptide, lane 3 and 4 with SPY393 with FXYD2-gamma-a blocking peptide and lane 5 and 6 with SPY393 without blocking peptide.
- C Western blot analysis was performed on total cellular extracts of CAPAN-2 cells (lane 1), PANC-1 cells (lane 2), AD293 cells (lane 3), INS-1E cells (lane 4) and dispersed rat islets control (lane 5, 8) and exposed to cytokines for 24 h (lane 6, 9), marker (lane 7), rat kidney positive control (lane 10). The lower arrow marks FXYD2-gamma-a expression detected by SPY393, the upper arrow marks beta-actin detected with a polyclonal rabbit anti-beta-actin.
- D Western blot analysis was performed on total cellular extracts of INS1E cells exposed for 24 h in control condition (lane 1), or to IL1beta (lane 2), IL1 beta+IFNgamma (lane 3), IFNgamma alone (lane 4) and similarly on total cellular extracts of AR42J cells exposed for 24 h in control condition (lane 5), or to IL1beta (lane 6), IL1 beta+IFNgamma (lane 7), IFN-gamma alone (lane 8), marker (lane 9) and rat kidney total cellular extract (lane 10). The lower arrow marks FXYD2-gamma-a expression detected by SPY393, the upper arrow marks beta-actin detected with a polyclonal rabbit anti-beta-actin. The blots are representative of 3-4 independent experiments.

The use of two separate cell-lines or cell-types that do and do not express the SPYone biomarker enables the identification of small molecules that specifically bind to the SPYone biomarker and which will be usefull as tracers for e.g. PET, PET-CT or SPECT analysis. The means for screening small molecules specific for binding with the SPYone-positive cells and not for SPYone-negative cells are well known in the art.

For example, a phage display experiment will be done to identify peptides binding to FXYD2, these peptides will be labeled and used to perform a biodistribution analysis. Alternatively, a chemical compound library will be screened for compounds binding specifically to FXYD2, this compound will be labeled and used to perform a biodistribution analysis. In addition, small antibody fragment "Nanobodies" (Ablynx NV) libraries, humanized single chain Fv libraries could be screened.

REFERENCES

Abramowitz J, Grenet D, Birnbaumer M, Torres H N, Birnbaumer L. XLalphas, the extra-long form of the alpha-subunit of the Gs G protein, is significantly longer than suspected, and so is its companion Alex. Proc Natl Acad Sci USA. 2004 Jun. 1; 101(22):8366-71. PMID: 15148396

Anlauf M, Eissele R, Schäfer M K, Eiden L E, Arnold R, Pauser U, Klöppel G, Weihe E. Expression of the two isoforms of the vesicular monoamine transporter (VMAT1 and VMAT2) in the endocrine pancreas and pancreatic endocrine tumors. J Histochem Cytochem. 2003 August; 51(8):1027-40. PMID: 12871984

Bastepe M, Gunes Y, Perez-Villamil B, Hunzelman J, Weinstein L S, Jüppner H. Receptor-mediated adenylyl cyclase activation through XLalpha(s), the extra-large variant of the stimulatory G protein alpha-subunit. Mol Endocrinol. 2002 August; 16(8):1912-9. PMID: 12145344

Bartoov-Shifman R, Ridner G, Bahar K, Rubins N, Walker M D. Regulation of the gene encoding GPR40, a fatty acid receptor expressed selectively in pancreatic beta cells. J Biol Chem. 2007 Aug. 10; 282(32):23561-71. PMID: 17525159

Brogren C H, Hirsch F, Wood P, Druet P, Poussier P. Production and characterization of a monoclonal islet cell surface autoantibody from the BB rat. Diabetologia. 1986 May; 29(5):330-3. PMID: 3522331

Buschard K, Brogren C H, Ropke C, Rygaard J. Antigen expression of the pancreatic beta-cells is dependent on their functional state, as shown by a specific, BB rat monoclonal autoantibody IC2. APMIS. 1988 April; 96(4):342-6. PMID: 3285866

Caohuy H, Srivastava M, Pollard H B. Membrane fusion protein synexin (annexin VII) as a Ca2+/GTP sensor in exocytotic secretion. Proc Natl Acad Sci USA. 1996 Oct. 1; 93(20):10797-802. PMID: 8855260

Chimienti F, Devergnas S, Favier A, Seve M. Identification and cloning of a beta-cell-specific zinc transporter, ZnT-8, localized into insulin secretory granules. Diabetes. 2004 September; 53(9):2330-7. PMID: 15331542

Chimienti F, Devergnas S, Pattou F, Schuit F, Garcia-Cuenca R, Vandewalle B, Kerr-Conte J, Van Lommel L, Grunwald D, Favier A, Seve M. In vivo expression and functional characterization of the zinc transporter ZnT8 in glucose-induced insulin secretion. J Cell Sci. 2006 Oct. 15; 119(Pt 20):4199-206. PMID: 16984975

Chu Z L, Jones R M, He H, Carroll C, Gutierrez V, Lucman A, Moloney M, Gao H, Mondala H, Bagnol D, Unett D, Liang Y, Demarest K, Semple G, Behan D P, Leonard J. A role for beta-cell-expressed G protein-coupled receptor 119 in glycemic control by enhancing glucose-dependent insulin release. Endocrinology. 2007 June; 148(6):2601-9. PMID: 17289847 de Lonlay P, Giurgea I, Sempoux C, Touati G, Jaubert F, Rahier J, Ribeiro M, Brunelle F, Nihoul-Fékété C, Robert J J, Saudubray J M, Stanley C, Bellanné-Chantelot C. Dominantly inherited hyperinsulinaemic hypoglycaemia. J Inherit Metab Dis. 2005; 28(3):267-76. PMID: 15868462 de Lonlay P, Simon-Carre A, Ribeiro M J, Boddaert N, Giurgea I, Laborde K, Bellanné-Chantelot C, Verkarre V, Polak M, Rahier J, Syrota A, Seidenwurm D, Nihoul-Fékété C, Robert J J, Brunelle F, Jaubert F. Congenital hyperinsulinism: pancreatic [18F]fluoro-L-dihydroxyphenylalanine (DOPA) positron emission tomography and immunohistochemistry study of DOPA decarboxylase and insulin secretion. J Clin Endocrinol Metab. 2006 March; 91(3): 933-40. PMID: 16403819

Egerod K L, Hoist B, Petersen P S, Hansen J B, Mulder J, Hökfelt T, Schwartz T W. GPR39 splice variants versus antisense gene LYPD1: expression and regulation in gastrointestinal tract, endocrine pancreas, liver, and white adipose tissue. Mol Endocrinol. 2007 July; 21(7):1685-98. PMID: 17488974

Evgenov N V, Medarova Z, Dai G, Bonner-Weir S, Moore A. In vivo imaging of islet transplantation. Nat Med. 2006 January; 12(1):144-8. PMID: 16380717

Hintsch G, Zurlinden A, Meskenaite V, Steuble M, Fink-Widmer K, Kinter J, Sonderegger P. The calsyntenins—a family of postsynaptic membrane proteins with distinct neuronal expression patterns. Mol Cell Neurosci. 2002 November; 21(3):393-409. PMID: 12498782

Holmskov U, Mollenhauer J, Madsen J, Vitved L, Gronlund J, Tornoe I, Kliem A, Reid K B, Poustka A, Skjodt K. Cloning of gp-340, a putative opsonin receptor for lung surfactant protein D. Proc Natl Acad Sci USA. 1999 Sep. 14; 96(19): 10794-9. PMID: 10485905

Flodgren E, Olde B, Meidute-Abaraviciene S, Winzell M S, Ahrén B, Salehi A. GPR40 is expressed in glucagon producing cells and affects glucagon secretion. Biochem Biophys Res Commun. 2007 Mar. 2; 354(1):240-5. PMID: 17214971

Fredriksson R, Höglund P J, Gloriam D E, Lagerström M C, Schiöth H B. Seven evolutionarily conserved human rhodopsin G protein-coupled receptors lacking close relatives. FEBS Lett. 2003 Nov. 20; 554(3):381-8. PMID: 14623098

Fukui K, Yang Q, Cao Y, Takahashi N, Hatakeyama H, Wang H, Wada J, Zhang Y, Marselli L, Nammo T, Yoneda K, Onishi M, Higashiyama S, Matsuzawa Y, Gonzalez F J, Weir G C, Kasai H, Shimomura I, Miyagawa J, Wollheim C B, Yamagata K. The HNF-1 target collectrin controls insulin exocytosis by SNARE complex formation. Cell Metab. 2005 December; 2(6):373-84. PMID: 16330323

Gotthardt M, Fischer M, Naeher I, Holz J B, Jungclas H, Fritsch H W, Béhé M, Göke B, Joseph K, Behr T M. Use of the incretin hormone glucagon-like peptide-1 (GLP-1) for the detection of insulinomas: initial experimental results. Eur J Nucl Med Mol Imaging. 2002 May; 29(5):597-606. PMID: 11976797

Hardy O T, Hernandez-Pampaloni M, Saffer J R, Scheuermann J S, Ernst L M, Freifelder R, Zhuang H, Macmullen C, Becker S, Adzick N S, Divgi C, Alavi A, Stanley C A. Accuracy of [18F]Fluorodopa Positron Emission Tomography for Diagnosing and Localizing Focal Congenital Hyperinsulinism. J Clin Endocrinol Metab. 2007 December; 92(12):4706-4711. PMID: 17895314

Kauhanen S, Seppänen M, Minn H, Gullichsen R, Salonen A, Alanen K, Parkkola R, Solin O, Bergman J, Sane T, Salmi J, Välimäki M, Nuutila P. Fluorine-18-L-dihydroxyphenylalanine (18F-DOPA) positron emission tomography as a tool to localize an insulinoma or beta-cell hyperplasia in adult patients. J Clin Endocrinol Metab. 2007 April; 92(4): 1237-44. PMID: 17227804

Kehlenbach R H, Matthey J, Huttner W B. XL alpha s is a new type of G protein. Nature. 1994 Dec. 22-29; 372(6508): 804-9. PMID: 7997272

Klemke M, Kehlenbach R H, Huttner W B. Two overlapping reading frames in a single exon encode interacting proteins—a novel way of gene usage. EMBO J. 2001 Jul. 16; 20(14):3849-60. PMID: 11447126

Konecna A, Frischknecht R, Kinter J, Ludwig A, Steuble M, Meskenaite V, Indermühle M, Engel M, Cen C, Mateos J M, Streit P, Sonderegger P. Calsyntenin-1 docks vesicular cargo to kinesin-1. Mol Biol Cell. 2006 August; 17(8): 3651-63. PMID: 16760430

Kung M P, Hou C, Goswami R, Ponde D E, Kilbourn M R, Kung H F. Characterization of optically resolved 9-fluoropropyl-dihydrotetrabenazine as a potential PET imaging agent targeting vesicular monoamine transporters. Nucl Med Biol. 2007 April; 34(3):239-46. PMID: 17383573

Madiraju S R, Poitout V. G protein-coupled receptors and insulin secretion: 119 and counting. Endocrinology. 2007 June; 148(6):2598-600. PMID: 17507578

Maffei A, Liu Z, Witkowski P, Moschella F, Del Pozzo G, Liu E, Herold K, Winchester R J, Hardy M A, Harris P E. Identification of tissue-restricted transcripts in human islets. Endocrinology. 2004 October; 145(10):4513-21. PMID: 15231694

Magendzo K, Shirvan A, Cultraro C, Srivastava M, Pollard H B, Burns A L. Alternative splicing of human synexin mRNA in brain, cardiac, and skeletal muscle alters the unique N-terminal domain. J Biol Chem. 1991 Feb. 15; 266(5):3228-32. PMID: 1825209

Malaisse W J, Damhaut P, Malaisse-Lagae F, Ladriere L, Olivares E, Goldman S. Fate of 2-deoxy-2-[18F]fluoro-D-glucose in control and diabetic rats. Int J Mol Med. 2000 May; 5(5):525-32. PMID: 10762657

Medarova Z, Evgenov N V, Dai G, Bonner-Weir S, Moore A. In vivo multimodal imaging of transplanted pancreatic islets. Nat Protoc. 2006; 1(1):429-35. PMID: 17406265

Medarova Z, Castillo G, Dai G, Bolotin E, Bogdanov A, Moore A. Noninvasive magnetic resonance imaging of microvascular changes in type 1 diabetes. Diabetes. 2007 November; 56(11):2677-82. PMID: 17682091

Mollenhauer J, Wiemann S, Scheurlen W, Korn B, Hayashi Y, Wilgenbus K K, von Deimling A, Poustka A. DMBT1, a new member of the SRCR superfamily, on chromosome 10q25.3-26.1 is deleted in malignant brain tumours. Nat Genet. 1997 September; 17(1):32-9. PMID: 9288095

Moore A, Bonner-Weir S, Weissleder R. Noninvasive in vivo measurement of beta-cell mass in mouse model of diabetes. Diabetes. 2001 October; 50(10):2231-6. PMID: 11574403

Moore A, Grimm J, Han B, Santamaria P. Tracking the recruitment of diabetogenic CD8+ T-cells to the pancreas in real time. Diabetes. 2004 June; 53(6):1459-66. PMID: 15161749

Mueller W, Mollenhauer J, Stockhammer F, Poustka A, von Deimling A. Rare mutations of the DMBT1 gene in human astrocytic gliomas. Oncogene. 2002 Aug. 29; 21(38):5956-9. PMID: 12185598

Nakajo M, Jinnouchi S, Fukukura Y, Tanabe H, Tateno R, Nakajo M. The efficacy of whole-body FDG-PET or PET/CT for autoimmune pancreatitis and associated extrapancreatic autoimmune lesions. Eur J Nucl Med Mol Imaging. 2007 December; 34(12):2088-95. PMID: 17713765

Nagase T, Kikuno R, Ishikawa K, Hirosawa M, Ohara O. Prediction of the coding sequences of unidentified human genes. XVII. The complete sequences of 100 new cDNA clones from brain which code for large proteins in vitro. DNA Res. 2000 Apr. 28; 7(2)143-50. PMID: 10819331

Otonkoski T, Näntö-Salonen K, Seppänen M, Veijola R, Huopio H, Hussain K, Tapanainen P, Eskola O, Parkkola R, Ekström K, Guiot Y, Rahier J, Laakso M, Rintala R, Nuutila P, Minn H. Noninvasive diagnosis of focal hyperinsulinism of infancy with [18F]-DOPA positron emission tomography. Diabetes. 2006 January; 55(1):13-8. PMID: 16380471

Overton H A, Babbs A J, Doel S M, Fyfe M C, Gardner L S, Griffin G, Jackson H C, Procter M J, Rasamison C M, Tang-Christensen M, Widdowson P S, Williams G M, Reynet C. Deorphanization of a G protein-coupled receptor for oleoylethanolamide and its use in the discovery of small-molecule hypophagic agents. Cell Metab. 2006 March; 3(3):167-75. PMID: 16517404

Pasolli H A, Klemke M, Kehlenbach R H, Wang Y, Huttner W B. Characterization of the extra-large G protein alpha-subunit XLalphas. I. Tissue distribution and subcellular localization. J Biol Chem. 2000 Oct. 27; 275(43):33622-32. PMID: 10931823

Palmer R E, Lee S B, Wong J C, Reynolds P A, Zhang H, Truong V, Oliner J D, Gerald W L, Haber D A. Induction of BAIAP3 by the EWS-WT1 chimeric fusion implicates regulated exocytosis in tumorigenesis. Cancer Cell. 2002 December; 2(6):497-505. PMID: 12498718

Pineda M, Fernandez E, Torrents D, Estévez R, López C, Camps M, Lloberas J, Zorzano A, Palacin M. Identification of a membrane protein, LAT-2, that Co-expresses with 4F2 heavy chain, an L-type amino acid transport activity with broad specificity for small and large zwitterionic amino acids. J Biol Chem. 1999 Jul. 9; 274(28):19738-44. PMID: 10391915

Pinho M J, Gomes P, Serrão M P, Bonifácio M J, Soares-da-Silva P. Organ-specific overexpression of renal LAT2 and enhanced tubular L-DOPA uptake precede the onset of hypertension. Hypertension. 2003 October; 42(4):613-8. PMID: 12975385

Pinho M J, Serrão M P, Gomes P, Hopfer U, Jose P A, Soares-da-Silva P. Over-expression of renal LAT1 and LAT2 and enhanced L-DOPA uptake in SHR immortalized renal proximal tubular cells. Kidney Int. 2004 July; 66(1):216-26. PMID: 15200428

Quiñones H, Collazo R, Moe O W. The dopamine precursor L-dihydroxyphenylalanine is transported by the amino acid transporters rBAT and LAT2 in renal cortex. Am J Physiol Renal Physiol. 2004 July; 287(1):F74-80. PMID: 15180924

Rana R S, Kowluru A, MacDonald M J. Enzymes of phospholipid metabolism in rat pancreatic islets: subcellular distribution and the effect of glucose and calcium. J Cell Biochem. 1986; 32(2):143-50. PMID: 3023405

Ribeiro M J, Boddaert N, Delzescaux T, Valayannopoulos V, Bellanné-Chantelot C, Jaubert F, Verkarre V, Nihoul-Fékété C, Brunelle F, De Lonlay P. Functional imaging of the pancreas: the role of [18F]fluoro-L-DOPA PET in the diagnosis of hyperinsulinism of infancy. Endocr Dev. 2007; 12:55-66. PMID: 17923769

Rinta-Valkama J, Palmeri T, Lassila M, Holthöfer H. Podocyte-associated proteins FAT, alpha-actinin-4 and filtrin are expressed in Langerhans islets of the pancreas. Mol Cell Biochem. 2007 January; 294(1-2):117-25. PMID: 16841182

Ruf J, Lopez Hänninen E, Böhmig M, Koch I, Denecke T, Plotkin M, Langrehr J, Wiedenmann B, Felix R, Amthauer H. Impact of FDG-PET/MRI image fusion on the detection of pancreatic cancer. Pancreatology. 2006; 6(6):512-9. PMID: 17106215

Saito S, Sakagami H, Tonosaki A, Kondo H. Localization of mRNAs for CDP-diacylglycerol synthase and phosphatidylinositol synthase in the brain and retina of developing and adult rats. Brain Res Dev Brain Res. 1998 Sep. 10; 110(1):21-30. PMID: 9733908

Sakamoto Y, Inoue H, Kawakami S, Miyawaki K, Miyamoto T, Mizuta K, Itakura M. Expression and distribution of Gpr119 in the pancreatic islets of mice and rats: predominant localization in pancreatic polypeptide-secreting PP-cells. Biochem Biophys Res Commun. 2006 Dec. 15; 351(2):474-80. PMID: 17070774

Samli K N, McGuire M J, Newgard C B, Johnston S A, Brown K C. Peptide-mediated targeting of the islets of Langerhans. Diabetes. 2005 July; 54(7):2103-8. PMID: 15983211

Seve M, Chimienti F, Devergnas S, Favier A. In silico identification and expression of SLC30 family genes: an expressed sequence tag data mining strategy for the characterization of zinc transporters' tissue expression. BMC Genomics. 2004 May 23; 5(1):32. PMID: 15154973

Simpson N R, Souza F, Witkowski P, Maffei A, Raffo A, Herron A, Kilbourn M, Jurewicz A, Herold K, Liu E, Hardy M A, Van Heertum R, Harris P E. Visualizing pancreatic beta-cell mass with [11C]DTBZ. Nucl Med Biol. 2006 October; 33(7):855-64. PMID: 17045165

Srivastava M, Atwater I, Glasman M, Leighton X, Goping G, Caohuy H, Miller G, Pichel J, Westphal H, Mears D, Rojas E, Pollard H B. Defects in inositol 1,4,5-trisphosphate receptor expression, Ca(2+) signaling, and insulin secretion in the anx7(+/−) knockout mouse. Proc Natl Acad Sci USA. 1999 Nov. 23; 96(24):13783-8. PMID: 10570150

Srivastava M, Eidelman O, Leighton X, Glasman M, Goping G, Pollard H B. Anx7 is required for nutritional control of gene expression in mouse pancreatic islets of Langerhans. Mol Med. 2002 December; 8(12):781-97. PMID: 12606813

Souza F, Simpson N, Raffo A, Saxena C, Maffei A, Hardy M, Kilbourn M, Goland R, Leibel R, Mann J J, Van Heertum R, Harris P E. Longitudinal noninvasive PET-based beta cell mass estimates in a spontaneous diabetes rat model. J Clin Invest. 2006 June; 116(6):1506-13. PMID: 16710474

Sun C, Kilburn D, Lukashin A, Crowell T, Gardner H, Brundiers R, Diefenbach B, Carulli J P. Kirrel2, a novel immunoglobulin superfamily gene expressed primarily in beta cells of the pancreatic islets. Genomics. 2003 August; 82(2):130-42. PMID: 12837264

Sweet I R, Cook D L, Lernmark A, Greenbaum C J, Krohn K A. Non-invasive imaging of beta cell mass: a quantitative analysis. Diabetes Technol Ther. 2004 October; 6(5):652-9. PMID: 15628819

Timpson P, Wilson A S, Lehrbach G M, Sutherland R L, Musgrove E A, Daly R J. Aberrant expression of cortactin in head and neck squamous cell carcinoma cells is associated with enhanced cell proliferation and resistance to the epidermal growth factor receptor inhibitor gefitinib. Cancer Res. 2007 Oct. 1; 67(19):9304-14. PMID: 17909038

Vogt L, Schrimpf S P, Meskenaite V, Frischknecht R, Kinter J, Leone D P, Ziegler U, Sonderegger P. Calsyntenin-1, a proteolytically processed postsynaptic membrane protein with a cytoplasmic calcium-binding domain. Mol Cell Neurosci. 2001 January; 17(1):151-66. PMID: 11161476

Watson W D, Srivastava M, Leighton X, Glasman M, Faraday M, Fossam L H, Pollard H B, Verma A. Annexin 7 mobilizes calcium from endoplasmic reticulum stores in brain. Biochim Biophys Acta. 2004 Dec. 6; 1742(1-3):151-60. PMID: 15590065

Wenzlau J M, Juhl K, Yu L, Moua O, Sarkar S A, Gottlieb P, Rewers M, Eisenbarth G S, Jensen J, Davidson H W, Hutton J C. The cation efflux transporter ZnT8 (Slc30A8) is a major autoantigen in human type 1 diabetes. Proc Natl Acad Sci USA. 2007 Oct. 23; 104(43):17040-5. PMID: 17942684

Wild D, Béhé M, Wicki A, Storch D, Waser B, Gotthardt M, Keil B, Christofori G, Reubi J C, Mäcke H R. [Lys40(Ahx-DTPA-111In)NH2]exendin-4, a very promising ligand for glucagon-like peptide-1 (GLP-1) receptor targeting. J Nucl Med. 2006 December; 47(12):2025-33. PMID: 17138746

Ylipaasto P, Kutlu B, Rasilainen S, Rasschaert J, Salmela K, Teerijoki H, Korsgren O, Lahesmaa R, Hovi T, Eizirik D L, Otonkoski T, Roivainen M. Global profiling of coxsackievirus- and cytokine-induced gene expression in human pancreatic islets. Diabetologia. 2005 August; 48(8):1510-22. PMID: 15991020

Yu D H, Fan W, Liu G, Nguy V, Chatterton J E, Long S, Ke N, Meyhack B, Bruengger A, Brachat A, Wong-Staal F, Li Q X. PHTS, a novel putative tumor suppressor, is involved in the transformation reversion of HeLaHF cells independently of the p53 pathway. Exp Cell Res. 2006 Apr. 1; 312(6):865-76. PMID: 16413018

The invention claimed is:

1. A method for specifically detecting pancreatic beta cells in a sample of pancreatic tissue, the method comprising detecting an a-isoform of the gamma subunit of the Na, K-ATPase (FXYD2-gamma-a isoform) in the sample.

2. A method for specifically measuring pancreatic beta-cell mass, the method comprising:
   visualizing pancreatic beta cells in a sample of pancreatic tissue utilizing a labelled molecule specifically binding to FXYD2-gamma a-isoform;
   quantifying the amount of labelled pancreatic beta cells in the sample; and
   measuring pancreatic beta cell mass determining the percent of pancreatic beta cells in the total amount of pancreatic cells present in the sample.

3. A method for following up the success of the transplantation of pancreatic beta cells in a subject, the method comprising:
   visualizing pancreatic beta cells in a sample of pancreatic tissue from the subject utilizing a labelled molecule specifically binding to FXYD2-gamma a-isoform;
   quantifying the amount of labelled pancreatic beta cells in the sample;

measuring pancreatic beta cell mass by determining the percent of pancreatic beta cells in the total amount of pancreatic cells present in the sample; and determining the success of the transplantation by tracking the pancreatic beta cell mass in the subject over time.

4. A method for specifically detecting pancreatic beta cells in a sample of pancreatic tissue, the method comprising: detecting a marker selected from the group consisting of: FXYD2-gamma a-isoform, Guanine nucleotide-binding G(s) alpha subunit isoform extra-large (GNAS-XLas), Guanine nucleotide-binding G(s) alpha subunit isoform encoded by XL-exon (GNAS-Alex), CDP-diacylglycerol-inositol 3-phosphatidyltransferase (CDIPT), vesicle amine transport protein 1 homolog (VAT1), Calsyntenin 1 (CLSTN1), solute carrier family 7, member 5 (SLC7A5), cortactin (CTTN), BAI1-associated protein 3 (BAIAP3), LY6/PLAUR: domain containing 1 (LLYPD1), Annexin A7 (ANXA7), deleted in malignant brain tumors 1 (DMBT1), RIKEN cDNA 2310057J16 gene (KIAA1543), and solute carrier family 7, member 8 (SLC7A8) in the sample.

* * * * *

UNITED STATES PATENT AND TRADEMARK OFFICE
CERTIFICATE OF CORRECTION

PATENT NO. : 8,425,878 B2  
APPLICATION NO. : 12/735731  
DATED : April 23, 2013  
INVENTOR(S) : Decio L. Eizirik et al.

Page 1 of 1

It is certified that error appears in the above-identified patent and that said Letters Patent is hereby corrected as shown below:

On the title page:

In ITEM (73) Assignee:   change "Assignee: Universite Libre de Bruxelles, Brussels (BE)" to  
--Assignees: Universite Libre de Bruxelles, Brussels (BE), Eurogentec, Seraing (BE), and Institute for Systems Biology, Seattle, WA (US)--

Signed and Sealed this  
Seventeenth Day of February, 2015

Michelle K. Lee  
*Deputy Director of the United States Patent and Trademark Office*